(12) United States Patent
Pentland et al.

(10) Patent No.: US 8,852,642 B2
(45) Date of Patent: Oct. 7, 2014

(54) GLYPHOSATE FORMULATION

(75) Inventors: Philip Pentland, Flemington (AU); Anthony Flynn, Wandana Heights (AU); Abhinetiri Maharaj, Greenvale (AU)

(73) Assignee: Eureka! AgResearch (Vic) Pty Ltd, Victoria (AU)

( * ) Notice: Subject to any disclaimer, the term of this patent is extended or adjusted under 35 U.S.C. 154(b) by 20 days.

(21) Appl. No.: 13/514,649

(22) PCT Filed: Dec. 8, 2010

(86) PCT No.: PCT/AU2010/001663
§ 371 (c)(1),
(2), (4) Date: Aug. 10, 2012

(87) PCT Pub. No.: WO2011/069202
PCT Pub. Date: Jun. 16, 2011

(65) Prior Publication Data
US 2012/0302443 A1 Nov. 29, 2012

(30) Foreign Application Priority Data
Dec. 8, 2009 (AU) ................................ 2009905979

(51) Int. Cl.
*A61K 9/14* (2006.01)
*A01N 57/18* (2006.01)
*A01N 57/20* (2006.01)

(52) U.S. Cl.
CPC ...................................... *A01N 57/20* (2013.01)
USPC .......................................... 424/489; 504/206

(58) Field of Classification Search
None
See application file for complete search history.

(56) References Cited

U.S. PATENT DOCUMENTS

| | | | |
|---|---|---|---|
| 5,047,079 A | 9/1991 | Djafar et al. | |
| 5,070,197 A | 12/1991 | Chin et al. | |
| 5,266,553 A | 11/1993 | Champion et al. | |
| 5,569,639 A * | 10/1996 | Beestman | 504/128 |
| 5,633,397 A | 5/1997 | Gillespie et al. | |
| 6,475,954 B2 * | 11/2002 | Hamroll et al. | 504/206 |
| 6,881,706 B1 | 4/2005 | Gustavsson | |
| 8,461,082 B2 * | 6/2013 | Pentland et al. | 504/206 |
| 2008/0194409 A1 | 8/2008 | Bernardini et al. | |
| 2009/0062123 A1 | 3/2009 | Quick et al. | |

FOREIGN PATENT DOCUMENTS

| | | | |
|---|---|---|---|
| WO | WO 9212637 | * | 8/1992 |
| WO | WO-03/013241 A1 | | 2/2003 |
| WO | WO-2004/019681 A2 | | 3/2004 |
| WO | WO-2007/143788 A1 | | 12/2007 |

* cited by examiner

*Primary Examiner* — Alton Pryor
(74) *Attorney, Agent, or Firm* — McCarter & English, LLP; Elizabeth A. Hanley; Yu Lu

(57) ABSTRACT

The present invention provides a solid glyphosate formulation comprising glyphosate acid and further comprising at least one agriculturally acceptable salt of glyphosate, wherein the glyphosate acid and the at least one glyphosate salt are in admixture and wherein the mole ratio of glyphosate acid to total glyphosate moieties in the formulation is at least 10%. Methods of preparing said formulations are also provided. The present invention further provides a method of removing unwanted foliage comprising administering a diluted form of a formulation according to the present invention.

46 Claims, 7 Drawing Sheets

US 8,852,642 B2

GLYPHOSATE FORMULATION

CROSS-REFERENCE TO RELATED APPLICATIONS

The present application is a U.S. national stage application filed under 35 U.S.C. 371, based on International Application No. PCT/AU2010/001663, filed on 8 Dec. 2010, which claims priority from Australian Provisional Application No. 2009905979, filed on 8 Dec. 2009, the content of which is incorporated herein by reference.

FIELD OF THE INVENTION

This invention relates to solid glyphosate compositions that comprise a high loading of glyphosate on an acid equivalent basis. Such compositions may be fully formulated compositions that include glyphosate-synergising adjuvants, and that have a herbicidal activity per unit glyphosate acid equivalent that is comparable with the herbicidal activity of standard liquid glyphosate formulations such as Round-up CT. Such compositions may also be tank-mix formulations that require the separate addition of the formulation and the glyphosate-synergising materials to a spray tank.

BACKGROUND

In the manufacture of glyphosate (N-phosphonyl methyl glycine), the acid form is precipitated from the reaction mixture and the resulting wet cake is reacted with an appropriate base to form a water soluble salt. The intermediate technical grade glyphosate free acid is poorly water soluble and is not used as a herbicide. The herbicidal composition of salts of glyphosate is then prepared from the salt as an aqueous solution concentrate and may contain adjuvants such as surfactants that reinforce the herbicidal effect of glyphosate.

There is an ongoing need to provide solid glyphosate formulations that contain higher levels of glyphosate on an acid equivalent (ae) basis—this is because such formulations are more convenient for the farmer to use, require less packaging to deliver and provide a means of achieving product differentiation.

Some highly loaded fully formulated solid glyphosate compositions that have been developed include the following:

U.S. Pat. No. 5,633,397 (Gillespie et al., filed 1995) describes the preparation of mono-ammonium glyphosate via a gas-solid reaction system. The reaction product dissolves readily and completely in water and can be used to prepare a highly-loaded, adjuvant-containing (ie fully formulated) glyphosate composition. The maximum glyphosate loading in a fully formulated solid glyphosate composition in this patent (example 2) comprises 80% mono-ammonium glyphosate, which corresponds to 72.5% glyphosate acid equivalent (ae). This patent describes prior art related to the preparation of glyphosate salts, including U.S. Pat. No. 5,047,079 (isopropylamine salt), U.S. Pat. No. 5,070,197 (sodium salt), U.S. Pat. No. 5,266,553 (ammonia, alkylamine, hydroxylamine, alkali metal salts).

US application 20080194409 (Bernadini et al., filed 2006) describes a process for preparing mono-ammonium glyphosate salt wherein a Broensted base which supplies ammonium ions is added to glyphosate acid. Tight control is required over reaction conditions. This application notes that mono-sodium and mono-ammonium glyphosate salts are particularly suitable for making water-soluble glyphosate granules, and that the ammonium salt is particularly suitable as it is less hygroscopic, and thus more storage stable. This application notes that handling ammonia can be challenging with respect to corrosive hazard, gas containment and/or thermal hazard associated with the neutralisation exotherm. Examples 1, 2 and 3 in this application describe fully formulated glyphosate compositions having a glyphosate loading of 72% ae by weight—this is the maximum glyphosate ae loading achieved.

WO 92/12,637 describes a process wherein glyphosate acid is mixed in powder form and under anhydrous conditions with a solid base such as sodium acetate. In this case salt formation does not occur during the process, but rather when the granule is added to water in the spray tank before use.

"Monsanto do Brasil LTDA" in Brazil sells Roundup WG—this product contains 792.5 g/kg of glyphosate mono-ammonium salt, which is equivalent to 72% glyphosate ae. Most granular glyphosate formulations sold in Brazil, Canada, Australia and USA have loadings of 700 or 680 g/kg ae.

There is an ongoing need for fully formulated granular glyphosate compositions that comprise high loadings of glyphosate.

WO 2007/143788 (Pentland and Flynn, "Herbicidal Composition and Method for Removing Unwanted Foliage") describes a 2-pack method of preparing a spray tank mix of glyphosate comprising (a) providing glyphosate acid solid concentrate (glyphosate 95% pure, concentrate comprises 950 g/kg acid equivalent); (b) an alkaline composition and (c) adding the glyphosate acid concentrate to a diluted aqueous mixture of the alkaline composition. Whilst the glyphosate acid equivalent loading in one of the packs is very high (950 g/kg), the following constraints arise: (i) the second pack must comprise alkali and will generally comprise liquid alkali (probably in admixture with a glyphosate-synergising surfactant)—the requirement to transport acid and alkaline packs in close proximity is problematic; (ii) the requirement for the glyphosate-synergising surfactant to be compatible with the alkaline material can be problematic, and can limit the suitable glyphosate-synergising surfactants that can be used in the second pack; (iii) the order of addition of the 2 packs is critical for successful application of glyphosate; (iv) the rate of addition of the glyphosate concentrate is critical for successful application of glyphosate—in particular if the glyphosate concentrate is added too rapidly to the diluted alkaline spray water, some of the concentrate may accumulate on the bottom of the spray tank and may not be properly neutralised.

There is also an ongoing need for a 2-pack glyphosate formulation wherein the glyphosate acid-containing pack is at high loading, and wherein the order of addition of the packs to the spray water is not critical.

SUMMARY OF INVENTION

The present inventors have surprisingly found that glyphosate acid in relatively large amounts (ie in a molar ratio of 10% or greater) can be incorporated into solid compositions comprising glyphosate salts without adversely affecting the formulation or dissolution properties of the compositions. The present invention therefore provides formulations having a higher glyphosate acid equivalent loading than could be achieved by the methods of the prior art.

The invention therefore provides a solid glyphosate formulation comprising glyphosate acid and further comprising at least one agriculturally acceptable salt of glyphosate, wherein the glyphosate acid and the at least one glyphosate salt are in admixture and wherein the mole ratio of glyphosate acid to total glyphosate moieties in the formulation is at least 10%.

There is also provided a method of using the formulation, or a diluted form thereof, in removing unwanted foliage.

DETAILED DESCRIPTION OF THE INVENTION

Figure 1:
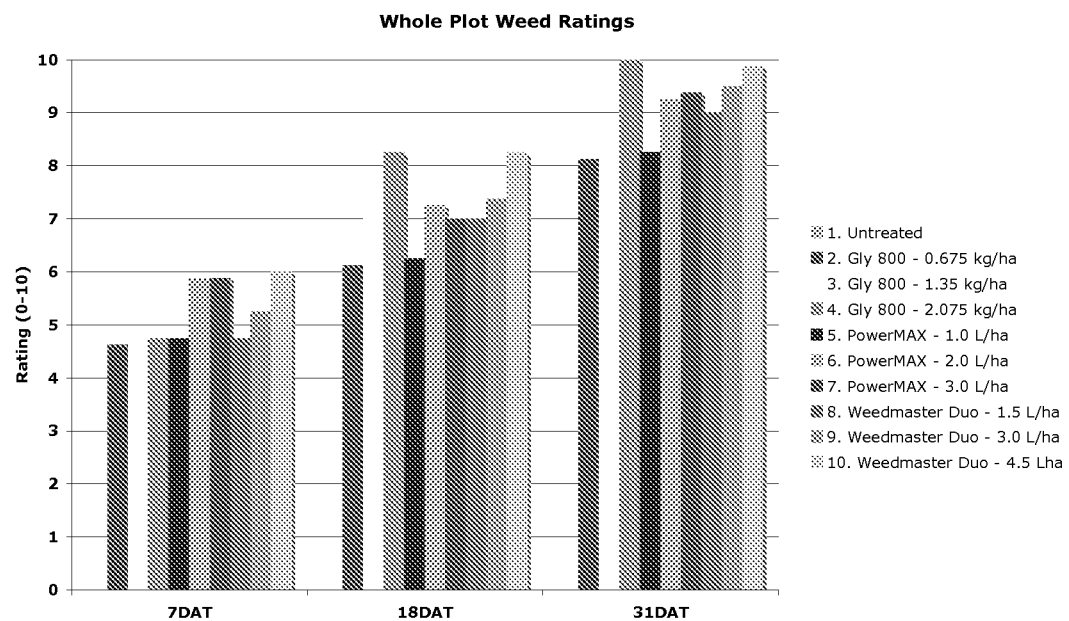
FIG. 1 illustrates whole plot weed phytotoxicity ratings for formulations according to the present invention when compared to the commercially available formulations PowerMAX and Weedmaster Duo.

As used herein the term "glyphosate acid" means glyphosate in the free acid form.

As used herein the term "glyphosate acid equivalent", "glyphosate ae", "acid equivalent" or "ae" refers to the weight of glyphosate present in a formulation calculated on the basis that all of the glyphosate is present in the acid form.

The invention provides a solid glyphosate formulation comprising glyphosate acid and further comprising at least one agriculturally acceptable salt of glyphosate, wherein the glyphosate acid and the at least one glyphosate salt are in uniform admixture and wherein the mole ratio of glyphosate free acid to total glyphosate moieties in the formulation is at least 10%.

In a preferred embodiment, the mole ratio of glyphosate acid to total glyphosate moieties is less than 50%, and is preferably less than 40%, and even more preferably less than 30%.

In another preferred embodiment, the glyphosate salt is monoammonium glyphosate, and the weight ratio of glyphosate acid to total glyphosate (acid equivalent) is in the range of 9-50%, preferably 15-40%, more preferably 22-35%.

The molecular weight of glyphosate acid is 169.1 and the molecular weight of glyphosate monoammonium salt is 186.1. For later reference, the molecular weight of glyphosate monopotassium salt is 207. Thus, for example, if all glyphosate in the formulation is present either in the acid form or in the monoammonium salt form, and if 10% of the total number of moles of glyphosate moieties comprise glyphosate acid, the following calculation may be used to establish the ratio of the weight of glyphosate acid to the total weight of glyphosate acid and the monoammonium glyphosate. Suppose we have one mole of glyphosate acid present and 9 moles of monoammonium glyphosate present (ie 10% mole ratio of acid). Then there exists 169.1 grams of glyphosate acid and 1674.9 grams (ie 9×186.1) of monoammonium glyphosate, giving a total weight of 1844 grams. In other words, the percent weight ratio of glyphosate acid to the total of glyphosate moieties is 169.1/1844×100, ie 9.17%.

In practice, glyphosate acid is available as a 95% strength material or a 98% strength material or similar, and it is necessary to adjust the weight of these materials by a purity factor to calculate the quantity of glyphosate present. Similar considerations apply to glyphosate monoammonium salts and other preformed salts.

The presence of the glyphosate free acid in the formulation allows for a higher loading of glyphosate ae than the use of agriculturally acceptable salts of glyphosate alone. In addition, the present inventors have surprisingly found that the formulations of the present invention readily dissolve in aqueous solution, thus allowing for ease of mixing before use in spray tanks and the like. The ease of dissolution also avoids the need for using the alkali composition required in WO 2007/143788 with all its attendant disadvantages. The formulation preferably consists of granules, preferably in the range of from 0.5 mm to 3 mm in length.

Preferably, the formulation is in the form of granules suitable for use in a spray tank. Such granular formulations are sold for farm use. The granules are combined with water in the spray tank, and if the granules are fully formulated, there is no need for other additives. However, if the granules do not contain glyphosate synergising materials, these may be separately added to the spray tank to achieve optimal performance.

In one embodiment, the formulation consists of a powder, and said powder may further be presented in a water soluble bag.

In order to be used effectively as herbicides, glyphosate formulations typically require the presence of one or more adjuvants, often surfactants, which enhance spray performance or the activity of the glyphosate. Other components may also be present, such as ammonium sulphate which acts as a processing aid and water conditioner.

Accordingly, the formulation optionally comprises one or more adjuvants.

The adjuvant may be of a type registered for use with glyphosate. Examples of suitable adjuvants are provided in WO 2007/143788, the disclosure of which is hereby incorporated by reference.

Preferably, the adjuvant comprises a glyphosate synergising surfactant. These have been discussed, for example, in U.S. Pat. No. 6,881,706, the disclosure of which is hereby included by reference.

More preferably, the glyphosate synergising surfactant is selected from the group consisting of cocobetaine cocoamidopropylbetaine, tallowamine-15-ethoxylate (eg the material sold as TERWET 3780, CAS 61791-26-2), alkylpolyglycosides, and alkyldiaminealkoxylates such as the material sold as TERWET 1221.

Cocobetaine is the reaction product of dimethylcoconut amine with chloroacetic acid. Coconut amine primarily consists of C12 and C14 primary amines.

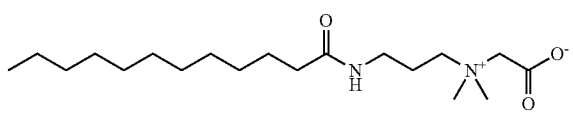 [SMILES: CCCCCCCCCCCC(=O)NCCC[N+](C)(C)CC(=O)[O-]]

Structure of Cocoamidopropyl Betaine

Cocobetaine is a registered agrochemical surfactant. However, cocoamidopropylbetaine is considerably cheaper and may therefore be a preferred adjuvant in solid glyphosate formulations of the present invention.

In one embodiment, the weight ratio of glyphosate synergising surfactant (dry weight basis) to glyphosate acid equivalent is at least 50:700, preferably is at least 80:700 and more preferably 100:700.

The formulation also optionally comprises other components which act as fillers, processing aids, or the like. Such additional components are well known to those skilled in the art.

In one embodiment, the formulation is fully formulated, which means that the formulation can be mixed with water and used directly as a herbicide, without the need to add additional components.

In a preferred embodiment, the at least one glyphosate salt is an agriculturally acceptable salt arising from the neutralisation of one or more labile glyphosate hydrogens. The salt may comprise cations chosen from the group consisting of ammonium, sodium, potassium, ethanolammonium, diethanolammonium, triethanolammonium, propylammonium, isopropylammonium, and trimesium cations.

Ammonium ions have a low molecular mass and therefore monoammonium glyphosate provides comparatively high loadings of glyphosate acid equivalent when mixed with glyphosate acid. Accordingly, in one embodiment, the salt comprises ammonium cations.

Preferably, the at least one glyphosate salt is monoammonium glyphosate, and the percent weight ratio of glyphosate acid to total glyphosate moieties is in the range 9-50%, 15-40%, more preferably 22-35%.

Preferably, the amount of glyphosate in the formulation calculated on an acid equivalent basis is at least 730 g/kg, more preferably at least 750 g/kg, more preferably at least 780 g/kg, and even more preferably at least 800 g/kg In another embodiment, the formulation comprising ammonium ions is suitable for use in a two-pack formulation. In two-pack formulations, glyphosate moieties and optionally one or more other components are provided in one pack and complementary components such as glyphosate synergising surfactants are provided in the other. In use, the contents of the two packs are individually added to water in the spray tank. The resulting liquid formulation is then suitable for use as a herbicide.

Preferably, the amount of glyphosate in the formulation calculated on an acid equivalent basis is at least 800 g/kg, preferably at least 850 g/kg, more preferably at least 880 g/kg, and even more preferably at least 900 g/kg.

In a particularly preferred embodiment, the order of addition of the two packs to the spray water is not critical, and the rate of addition of pack contents to spray water is also not critical.

More preferably, the formulation is a granule.

Although ammonium glyphosate provides for comparatively high loadings of glyphosate acid equivalent, other ions may be selected to provide desirable properties to the formulation. For example, the potassium ion provides granules with relatively high mechanical strength and hardness. This allows the formulation to be stored in bags rather than in bag-in-box packaging. Potassium ions are particularly useful in cases where betaine surfactants are used as adjuvants because the use of betaine surfactants in a glyphosate formulation tends to result in softer granules. The use of potassium glyphosate compensates for this softening.

Accordingly, in another embodiment, the at least one glyphosate salt comprises potassium cations.

Preferably, the amount of glyphosate in the formulation calculated on an acid equivalent basis is at least 600 g/kg, preferably at least 650 g/kg, more preferably at least 680 g/kg, even more preferably at least 700 g/kg, and most preferably at least 720 g/kg.

The potassium ions may be mixed with sodium ions. Such a mixture can retain the hardness associated with the use of potassium ions while also allowing for higher glyphosate acid equivalent loadings because the sodium ion has a lower molecular mass than potassium.

Accordingly, in one embodiment, the at least one glyphosate salt comprises potassium and sodium cations.

The potassium ions may also be mixed with ammonium ions.

In another preferred embodiment, when 1 gram of solid glyphosate formulation is mixed with 100 g of 1WHO hard water and passed through a 75 micron sieve, less than 0.02 g of residue (2%) is retained on the sieve. Details of the test used to determine retention of material on the sieve is provided subsequently in the context of a discussion of the CIPAC MT 179 test.

In another preferment, when 3.5 g of solid glyphosate formulation is mixed with 100 g of 2WHO hard water and passed through a 75 micron sieve, more than 0.03 g of residue is retained on the sieve.

In another preferment, the solid glyphosate formulation of the invention meets a first criterion in which 1 g of solid glyphosate formulation is mixed with 100 g of 1WHO hard water and passed through a 75 micron sieve with retention of less than 0.02 g residue on the sieve, and also meets a second criterion in which 3.5 g of solid glyphosate formulation is mixed with 100 g of 2WHO hard water and passed through a 75 micron sieve to leave more than 0.03 g of residue on the sieve.

In another preferment, the addition to distilled water of 1% glyphosate acid equivalent of fully formulated glyphosate granules according to the invention provides a final pH in the range 1.5-3.5, and more preferably in the range 2-3.

In Western Farm Express "Know your water quality in treating field bindweed", Sep. 1, 2007 (by Mick Canavan, UCCE Farm Adviser San Joaquim County California) the following guidelines are provided for using glyphosate— "Ideally the spray solution pH should be in the range 4.0-5.0 . . . " The present inventors have found that the formulations of the present invention are effective in spray solutions of higher acidity.

Accordingly, in another preferment, the addition to distilled water of 1% glyphosate acid equivalent of the glyphosate pack in a 2-pack system provides a final pH in the range 1.5-3.5, and more preferably in the range 2-3.

The present invention further provides a method of removing unwanted foliage comprising administering a diluted form of a solid glyphosate formulation according to the present invention to said foliage.

Also provided are methods of preparing solid glyphosate formulations in accordance with the invention.

For example, there is provided a method of preparing a solid glyphosate formulation comprising glyphosate acid and ammonium glyphosate wherein the mole ratio of glyphosate acid to total glyphosate moities in the formulation is at least 10%, said method comprising the step of mixing ammonium glyphosate with glyphosate acid.

There is also provided a method of preparing a solid glyphosate formulation comprising glyphosate acid and potassium glyphosate wherein the mole ratio of glyphosate acid to total glyphosate moieties in the formulation is at least 10%, said method comprising partially neutralising the glyphosate acid with potassium hydroxide.

In another embodiment, said formulation further comprises sodium glyphosate, and said method comprises the additional step of partially neutralising the glyphosate acid with sodium hydroxide.

In preparing solid glyphosate formulation according to the present invention, the glyphosate acid may be in the form of an 85% wetcake. Moisture in the wetcake may be at least partially removed in the granule drying stage.

Example 1

800 g/kg Glyphosate ae Granules (Denoted Gly 800)

| ingredient | Parts (weight) | Mole fraction of glyphosate moieties |
|---|---|---|
| Glyphosate acid (95%) | 230 | 0.27 |
| Mono-ammonium glyphosate (98%) | 653 | 0.73 |
| Cocoamido-propyl betaine (56% aq soln) | 205 | |
| Tap water | 500 | |
| Wet mass | 1588 | |
| Dry mass (after drying) | 1000 | |

The cocoamidopropylamidopropane was purchased as 35% aqueous solution and evaporated to achieve 56% aqueous solution.

The above ingredients were blended together in a food processor. The mixture was able to be deformed under pressure, without the occurrence of crumbling. The mixture was extruded through a small basket extruder (1 mm mesh) to form granules and some longer strands. The granules and strands were dried overnight in an oven at 40 deg C. and sieved to recover granules (1.0-2.0 mm length). In commercial use, the drying process may be carried out in a fluid bed dryer. The properties of the granules are given in the following table:

| method | Ambient storage (2 weeks) | Storage at 54 deg C. (2 weeks) | target |
|---|---|---|---|
| appearance | off-white free flowing granules | off-white free flowing granules | off-white free flowing granules |
| pH (protocol MT 171) - 1% solution | 3.0 | 3.1 | 2.8-3.2 |
| Dust content (protocol MT 179) | 0.1% | 0.1% | <1% 50 micron |
| Degree of dissolution and solution stability (protocol MT 176) sufficient formulation was added to water to make a 2.5% ae glyphosate solution | 0% | 0% | Max 2% on 75 micron screen |
| Packaging stability (PE bag in box) | No deterioration | No deterioration | No deterioration |

Protocols MT 171, 176, and 179 are CIPAC international standard protocols.

Example 2

Preparation of 1 WHO Standard Hard Water 0.304 g of anhydrous calcium chloride and 0.139 g of magnesium chloride hexahydrate were dissolved in distilled water and made up to 1 liter. This provided water with a hardness of 342 mg/L calculated as calcium carbonate. The hardness was checked using CIPAC method MT 73.

2 WHO standard hard water was obtained by adding twice the above quantity of salts to distilled water, and correspondingly for 3 WHO standard hard water, etc Example 3

Preparation of 2-Pack System with 900 g/kg Glyphosate Acid Equivalent Granules in the Glyphosate Pack The 2-pack system comprises a solid glyphosate pack and a second adjuvant pack which may be solid or liquid.

Example 3a

Glyphosate Pack with Partial Potassium Hydroxide Neutralisation

| | Amount (g/kg) | Mole fraction of glyphosate moieties |
|---|---|---|
| Glyphosate acid (95%) | 950 | 0.67 residual acid after reaction with KOH |
| KOH pellets (85%) | 117.6 (99.96) | After reaction forms 0.33 mole fraction of potassium glyphosate |
| water | 40 | |
| Total before drying | 1107.6 | |
| Total after drying | 1000 g/kg | |

In a first step, fine crystals of glyphosate were mixed with KOH pellets. Water was added and a thick slurry was produced, with evolution of heat. The slurry was dried at 60 deg C. until the resultant paste was dry enough to extrude (moisture content less than 5%, preferably between 4 and 5%). The extrudable paste was extruded into granules using a small basket extruder (Benchtop Granulator, Tsutsui Scientific Instruments Co Ltd, No 5752, Date 1995.3, made in Japan), and the granules were dried at 60 deg C. for 8 hrs. After drying, the granules were sieved and granules in the size range 1.0-2.0 mm were collected as product. In this example, the weight fraction of glyphosate acid (relative to the combined weight of glyphosate acid and glyphosate potassium salt) was approximately 61%.

Example 3b

Glyphosate Pack with Mixture of Acid and Ammonium Salt

| component | Amount (g/kg) | Mole fraction of glyphosate moieties |
|---|---|---|
| Glyphosate acid (95%) | 236.84 | 0.25 |
| Glyphosate mono-ammonium salt (98%) | 758.02 (742.86) | 0.75 |
| water | 40 | |
| Total before drying | 1034.86 | |
| Total after drying | 1000 | |

In a first step, fine glyphosate crystals were mixed with glyphosate mono-ammonium salt. Water was added to form an extrudable paste. The paste was extruded into granules using a small basket extruder as in example 3a, and the granules were dried at 60 deg C. for 8 hrs. After drying, the granules were sieved and granules in the size range 1.0-2.0 mm were collected as product. In this example, 75% by weight of glyphosate present was in salt form.

Example 3c

Adjuvant Pack (Non-Alkaline): Solid Pack

| component | Amount (g/kg) |
|---|---|
| Terwet 1221 | 200.0 |
| Urea (milled) | 200.0 |
| Geropon T/36 | 5.0 |
| Ammonium sulphate (milled) | 495 |
| Total | 1000 |

As a first step, Terwet 1221 (alkyl diamine alkoxylate, sold by Huntsman Australia) was molten at 60 deg C. in an oven. Urea pellets were passed through a hammer mill (BECY AG serial no 5080030021, supplied by TECO Australia Pty ltd) using a coarse mesh (2.5 mm) to obtain a fluffy powder. The molten Terwet 1221 was sprayed onto the milled urea and mixed to uniformity. During mixing, the temperature of the molten material decreased and fell below the melting point of the Terwet 1221 to form a wax. The mixture was allowed to harden at room temperature and was then passed through a 1.0 mm sieve. Lumps were broken up and passed through the sieve. Geropon T/36 (sodium polycarboxylate, CAS no 37199-81-8, sold by Rhodia in Australia) and milled ammonium sulfate were added to the Terwet-urea mixture. The Geropon T/36 acts as a drop size regulator and functions as a spray drift control agent. Then a small amount of water was added to the mixture and the resultant paste was extruded into granules with a basket extruder (as in previous examples).

The granules were dried overnight at room temperature and sieved to collect granules in the size range 1.0-2.0 mm.

Example 3d

Alternative Liquid Adjuvant Pack

| component | Amount (g/L) |
|---|---|
| Terwet 3780 | 940 |
| Butyl diglycol | 50 |

Terwet 3780 consisted of tallowamine-15-ethoxylate (liquid).

Note that other glyphosate tank-mix adjuvants may also be used in the adjuvant pack.

Example 4

Formulation Stability in Tap Water (CIPAC MT 179 Test)

A 100 ml measuring cylinder was taken and 50 ml tap water added at 25 deg C. Sufficient glyphosate pack material was added to the measuring cylinder to provide a 2.5% level of glyphosate in 100 ml, and (optionally) sufficient adjuvant pack material was added to the measuring cylinder to provide a 0.6% level of adjuvant in 100 ml. Additional water was added to make the liquor level in the measuring cylinder up to 100 ml at 25 deg C. The measuring cylinder was inverted 15 times by hand through an angle of 180 deg, and back to the original position. After 15 minutes standing, the liquor in the cylinder was poured through a 75 micron sieve. The filtrate was collected in a beaker and the residues were retained on the sieve were transferred to a weighed Petri dish. The transferred residues were dried in an oven and the amount after 15 minutes were measured. After 18 hrs the collected filtrate was passed through a 75 micron sieve and retained solids were transferred into a weighed Petri dish. The percentage of starting solids retained on a 75 micron sieve after 18 hrs standing was calculated by adding 15 minute and 18 hr results. Using materials prepared in example 3, the results were as follows:

| formulation | Initial appearance | pH of liquor | Solids after 18 hrs in tap water (sum of solids at 5 min and at 18 hrs) |
|---|---|---|---|
| F1 - Glyphosate pack with partial potassium hydroxide neutralisation (Example 3a) | cloudy | 1.66 | 4.3% |
| F2 - glyphosate pack with partial ammonia neutralisation (Example 3b) | Clear with trace solids | 2.3 | 0.3% |
| F3 - adjuvant Pack (see example 3c) | clear | 3.45 | 0.0% |
| F1 plus F3 (to achieve 2.5% glyphosate acid equiv from F1 and 0.12% Terwet 1221 from F3. | cloudy | 1.59 | 3.9% |
| F2 plus F3 (to achieve same ratios as above) | Minor trace of solids (less than F2 above) | 2.37 | 0.1% |

F1 was an unsatisfactory formulation with a high sieve test residue.

Note that the above test can be extended to stability in hard water such as 1 WHO hard water or 3 WHO hard water, by using the appropriate hard water in the measuring cylinder (instead of tap water).

Example 5

Solution pH at Various Mole Ratios of Glyphosate Acid and Glyphosate Monoammonium Salt, and in the Presence of Various Glyphosate-Synergising Surfactants

Example 5.1

Various mole ratios of glyphosate acid and glyphosate monoammonium salt were prepared in mixed powder form, granulated, and added to distilled water in a measuring cylinder to provide 1% w/w glyphosate acid equivalent liquors. The measuring cylinder was inverted as described in example 4. The pH values of the resultant liquors were measured, and the appearance of the liquors was also noted, and the results were as follows:

| Mole fraction of glyphosate in acid form (relative to total glyphosate moieties) | Ratio of moles of glyphosate acid to moles of glyphosate monoammonium salt | Weight ratio of glyphosate acid as a percent of total weight of glyphosate acid and glyphosate salt | Liquor pH (no glyphosate synergising surfactant present) | Appearance |
|---|---|---|---|---|
| 1.0 | 1:0 | 1.0 | 1.23 | cloudy |
| 0.8 | 4:1 | 0.784 | 1.46 | some fine solids |
| 0.75 | 3:1 | 0.732 | 1.58 | trace solids |
| 0.67 | 2:1 | 0.645 | 1.62 | trace solids |
| 0.50 | 1:1 | 0.476 | 1.83 | trace solids |
| 0.33 | 1:2 | 0.312 | 2.05 | trace solids |
| 0.25 | 1:3 | 0.232 | 2.27 | trace solids |
| 0.2 | 1:4 | 0.185 | 2.31 | clear |
| 0.0 | 0:1 | 0.0 | 3.68 | clear |

Example 5.2

The above experiment was repeated with the amendment that after adding the granule to the measuring cylinder, the glyphosate-synergising surfactant cocoamidobetaine was added in sufficient quantity to achieve a surfactant level of 0.12% in tap water.

| Ratio of moles of glyphosate acid to moles of glyphosate monoammonium salt | Liquor pH (Liquor contains 0.12% cocoamido betaine) | Appearance |
|---|---|---|
| 1:0 | 1.22 | cloudy |
| 4:1 | 1.50 | some fine solids |
| 3:1 | 1.60 | trace solids |
| 2:1 | 1.66 | trace solids |
| 1:1 | 1.87 | less solids |
| 1:2 | 2.14 | clear |
| 1:3 | 2.38 | clear |
| 1:4 | 2.41 | clear |
| 0:1 | 3.72 | clear |

Example 5.3

The above experiment was repeated with the amendment that after adding the granule to the measuring cylinder, the glyphosate-synergising surfactant Terwet 3780 (tallow amine-15-ethoxylate) was added in sufficient quantity to achieve a surfactant level of 0.12% in tap water. The final liquor was also passed through a 75 micron sieve. The sieve was dried and the percentage of initial material retained on the screen was noted.

| Ratio of moles of glyphosate acid to moles of glyphosate monoammonium salt | Liquor pH | Appearance | Solids retained on 75 micron sieve |
|---|---|---|---|
| 1:0 | 1.81 | cloudy | 21.0% |
| 4:1 | 2.01 | cloudy | 5.87% |
| 3:1 | 2.08 | trace solids | 3.5% |
| 2:1 | 2.17 | trace solids | 1.84% |
| 1:1 | 2.37 | trace solids | 1.83% |
| 1:2 | 2.63 | clear | 0% |
| 1:3 | 2.78 | clear | 0% |
| 1:4 | 2.82 | clear | 0% |
| 0:1 | 4.03 | clear | 0% |

It was assumed that the use of the same ingredients in a fully formulated granule (rather than two part addition) would give the same results.

Example 6

Composition and Sediment Values (75 Micron Screen) for a Range of Fully Formulated 800 g/kg Glyphosate Formulations at Various Mole Ratios of Glyphosate Acid to Glyphosate Mono-Ammonium Salt

| Mole ratio of acid to neutralized salt CHECK | 1 to 0 | 4 to 1 | 3 to 1 | 2 to 1 | 1 to 1 | 1 to 2 | 1 to 3 | 1 to 4 | 0 to 1 |
|---|---|---|---|---|---|---|---|---|---|
| Concentration of glyphosate acid equivalent | 800 g/kg | 800 g/kg | 800 g/kg | 800 g/kg | 800 g/kg | 800 g/kg | 800 g/kg | 798.5 g/kg | 779 g/kg |
| Glyphosate acid (95%) | 842.10 | 673.70 | 631.60 | 561.40 | 421.10 | 280.70 | 230.00 | 168.40 | 0.00 |
| Mono-ammonium glyphosate (98%) | 0.00 | 179.70 | 224.60 | 299.50 | 449.20 | 587.00 | 653.00 | 718.70 | 898.40 |
| Cocoamido-propyl betaine (56% aq soln) | 205.00 | 205.00 | 205.00 | 205.00 | 205.00 | 205.00 | 205.00 | 205.00 | 205.00 |
| Ammonium sulphate | 43.10 | 31.80 | 29.00 | 24.30 | 14.90 | 17.50 | 2.20 | 0.00 | 0.00 |
| Wet mass | 1090.20 | 1090.20 | 1090.20 | 1090.20 | 1090.20 | 1090.20 | 1090.20 | 1092.10 | 1103.40 |
| Dry mass (after drying) | 1000.00 | 1000.00 | 1000.00 | 1000.00 | 1000.00 | 1000.00 | 1000.00 | 1001.90 | 1013.20 |
| Sediment at 1% in 1 WHO hard water (Specification: residue ≤1%) | 15.5% | 12.3% | 10.7% | 6.7% | 2.5% | 1.7% | 0.0% | 0.0% | 0.0% |

| Mole ratio of acid to neutralized salt CHECK | 1 to 0 | 4 to 1 | 3 to 1 | 2 to 1 | 1 to 1 | 1 to 2 | 1 to 3 | 1 to 4 | 0 to 1 |
|---|---|---|---|---|---|---|---|---|---|
| Sediment at 3.5% in 1 WHO hard water (Specification: residue >0.1%) | 38.0% | 27.9% | 26.0% | 23.6% | 18.46% | 8.38% | 1.11% | 3.89% | 2.80% |
| Sediment in Tap Water | 21.0% | 5.87% | 3.50% | 1.84% | 1.83% | 0.0% | 0.0% | 0.0% | 0.0% |
| Sediment at 3.5% in 2 WHO hard water (Specification: residue >0.1%) | | | | | | | 5.71% | 4.65% | 1.37% |
| Sediment at 3.5% in 3 WHO hard water (Specification: residue >0.1%) | | | | | | | 5.10% | 3.32% | 2.28% |
| Sediment at 3.5% in 4 WHO hard water (Specification: residue >0.1%) | | | | | | | 4.32% | 4.65% | 1.92% |

Note that when the ratio of glyphosate acid to glyphosate salt was 0 to 1 (ie all glyphosate was in salt form, see column at right in the above table), the maximum amount of glyphosate acid equivalent that can be accommodated in the formulation (with a full loading of the adjuvant cocoamido-propyl betaine (56% aq soln) was 779 rather than 800 g/kg. In practice the achievable loading using all-salt formulations is even lower because some ammonium sulphate is needed as a processing aid. The above table shows that the presence of glyphosate acid as well as glyphosate salt (as taught by the current invention) is necessary to achieve high loadings of glyphosate. Even if glyphosate acid technical material is purchased at "greater than 97%" (rather than at greater than 95%) purity, the mixed acid-salt formulations of this invention will enable higher levels of glyphosate (on an acid-equivalent basis) to be included in a granular formulation.

Example 7

Composition and Sediment Values (75 Micron Screen) for a Range of Glyphosate Pack 900 g/kg Formulations (Part of a 2-Pack System) at Various Mole Ratios of Glyphosate Acid to Glyphosate Mono-Ammonium Salt Data is for addition of the glyphosate pack only to water of different hardnesses.

Example 8a 800 g/kg Glyphosate ae Granules (Denoted Gly 800) Using 98% Glyphosate Acid in Place of 95% Glyphosate Acid

| ingredient | parts |
|---|---|
| Glyphosate acid (98%) | 223 |
| Mono-ammonium glyphosate (98%) | 653 |
| Cocoamido-propyl betaine (56% aq soln) | 217.5 |
| Tap water | 500 |
| Wet mass | 1595.7 |
| Dry mass (after drying) | 1000 |

Because of the use of a higher purity of glyphosate, it was possible to include more surfactant in the formulation ie 217.5 rather than 205 parts.

| ingredient | parts |
|---|---|
| Glyphosate acid (98%) | 230 |
| Mono-ammonium glyphosate (98%) | 653 |
| Cocoamido-propyl betaine (56% aq soln) | 205 |
| Tap water | 500 |
| Wet mass | 1588 |
| Dry mass (after drying) | 1000 |

| Mole ratio of acid to neutralized salt CHECK | 1 to 0 | 4 to 1 | 3 to 1 | 2 to 1 | 1 to 1 | 1 to 2 | 1 to 3 | 1 to 4 | 0 to 1 |
|---|---|---|---|---|---|---|---|---|---|
| Gylphosate acid equivalent concentration g/kg | 900.00 | 900.00 | 900.00 | 900.00 | 900.00 | 900.00 | 900.00 | 900.00 | 890.48 |
| Glyphosate acid (95%) | 947.37 | 757.89 | 710.53 | 631.58 | 473.68 | 315.79 | 236.84 | 189.47 | 0.00 |
| Mono-ammonium glyphosate (98%) | 0.00 | 202.14 | 252.67 | 336.90 | 505.35 | 673.80 | 758.02 | 808.55 | 1010.69 |
| Ammonium sulphate (used in minor amounts as a filler to enable glyphosate acid equivalent to be 900 g/kg in each formulation) | 52.63 | 39.97 | 36.80 | 31.52 | 20.97 | 10.42 | 5.14 | 1.97 | 0.00 |
| Dry mass | 1000.00 | 1000.00 | 1000.00 | 1000.00 | 1000.00 | 1000.00 | 1000.00 | 1000.00 | 1010.69 |
| Sediment at 1% in 1 WHO hard water | 6.76% | 5.52% | 35.30% | 4.65% | 3.47% | 2.12% | 1.01% | 0.00% | 0.00% |
| Sediment at 3.5% in 1 WHO hard water | 47.36% | 33.85% | 35.30% | 28.15% | 18.79% | 9.80% | 9.11% | 6.61% | 0.00% |
| Sediment at 3.5% acid in 2 WHO hard water | | | | | | | 3.11% | 3.56% | 0.00% |
| Sediment at 3.5% acid in 3 WHO hard water | | | | | | | 4.22% | 3.89% | 0.00% |
| Sediment at 3.5% acid in 4 WHO hard water | | | | | | | 5.47% | 2.96% | 0.00% |

Because of the use of a higher purity of glyphosate, it was possible to include more glyphosate in the formulation ie 230 rather than 223 parts.

Example 8b 800 g/kg Glyphosate ae Granules (denoted Gly 800) Using 85% Glyphosate Acid Wet Cake in Place of 95% Glyphosate Acid

| ingredient | parts |
| --- | --- |
| Glyphosate acid (85%) | 257.1 |
| Mono-ammonium glyphosate (98%) | 653 |
| Cocoamido-propyl betaine (56% aq soln) | 205 |
| Tap water | 500 |
| Wet mass | 1615.1 |
| Dry mass (after drying) | 1000 |

The water component of the wet cake was substantially removed in the subsequent granule drying process.

Example 8c 800 g/kg Glyphosate Formulations

Formulations with Two Different Salts of Glyphosate
Method of Preparation:
1. Preparation of Glyphosate-sodium salt:
a. Dissolve NaOH in water to produce a 50% w/w solution
b. While mixing add to glyphosate acid—heat is evolved during this addition. A viscous slurry results.
c. Dry slurry at 70° C. overnight.
d. Crush glyphosate-sodium with a blender to produce a fine powder.
2. Preparation of Glyphosate-potassium salt:
a. Dissolve KOH in water to produce a 50% w/w solution
b. While mixing add to glyphosate acid—heat is evolved during this addition. A viscous slurry results.
c. Dry slurry at 70° C. overnight.
d. Crush glyphosate-sodium with a blender to produce a fine powder.
3. Preparation of granules
a. Blend together in a food processor glyphosate acid and glyphosate salt
b. While mixing, add enough water (10% w/w of total amount of dry ingredients) to form an extrudable dough.
c. Pass the dough through a basket extruder to produce granules of 1.0 mm diameter.
d. The extruded granules were dried at 60° C. for 12 hours.

The following formulation according to the present invention was found to be efficacious and practical to use and has satisfactory attrition resistance.

|  | g/kg | Mole fraction |
| --- | --- | --- |
| Glyphosate acid | 100.0 | 0.125 |
| Glyphosate-K | 428.86 | 0.4375 |
| Glyphosate-ammonium | 385.19 | 0.4375 |
| Cocoamido betaine (dry) | 85.96 |  |
| Total | 1000.0 |  |

The CIPAC Method MT 178 Attrition and Friability may be used to assess granule hardness.
Attrition resistance is satisfactory when it is >98%
1. Transfer 50 g of granules (w g) and equal amounts of glass beads (4.0 mm diameter) into a 750 ml glass bottle.
2. Close the bottle and place horizontally onto roller.
3. Rotate the bottle for 4500 revolutions at 125 rpm.
4. Assemble a 125 micron and 3.85 mm sieve on top of a receiver pan.
5. Transfer contents of glass bottle onto the coarse sieve.
6. Fit the lid of the sieve and place nest of sieves on a shaker.
7. Shake for 3 minutes
8. Determine the mass of material retained on the 125 micron sieve (a g).
9. Attrition resistance=a/w×100%

Example 9

Comparative Trial of Gly 800 (See Example 1) with Commercially Available Glyphosate Solutions

| Title | To evaluate Gly 800 for knockdown of grasses and various broadleaf weeds. To compare Gly 800 to the industry standards, Roundup PowerMAX and Weedmaster Duo. |
| --- | --- |
| Site | Jenkins Orchard 1211 High Street Road Wantirna South, Vic 352 |

Summary

A trial was established on an old orchard area where the trees had been removed, at Jenkins Orchard, Wantirna South, Victoria. There was a wide variety of grass and broadleaf weeds present.

Three products, experimental product, Gly 800, and the standard products, Roundup PowerMAX and Weedmaster Duo were applied at three rates of glyphosate per hectare; 540, 1080 and 1620 g glyphosate acid equivalent per hectare. The products were applied without the addition of a non-ionic wetting agent, with a total water volume of 123 L/ha.

The trial site was densely covered, including:
four grass species;
Couch (*Cynodon dactylon*), Kikuyu (*Pennisetum clandestinum*), Ryegrass Perennial (*Lolium perenne*) and Paspalum (*Paspalum dilatatum*), and
eight broadleaf weeds species;
Capeweed (*Arctotheca calendula*), Dandelion (*Taraxacum officinale*), Dock Curled (*Rumex crispus*), Flatweed (*Hypochaeris radicata*), Plantain (*Plantago lanceolata*), Soursob (*Oxalis pes-caprae*), Sub Clover (*Trifolium subterranean*), Creeping Speedwell (*Veronica persica*).

Gly 800 provided effective control of a range of grass and broadleaf weeds present in this trial.

Gly 800 achieved equivalent levels of weed control to the industry standards, Roundup PowerMAX and Weedmaster Duo, when applied at the same rate of glyphosate.

FIG. 1 illustrates whole plot weed phytotoxicity ratings for formulations according to the present invention when compared to the control PowerMAX and Weedmaster Duo.

Figure 2:
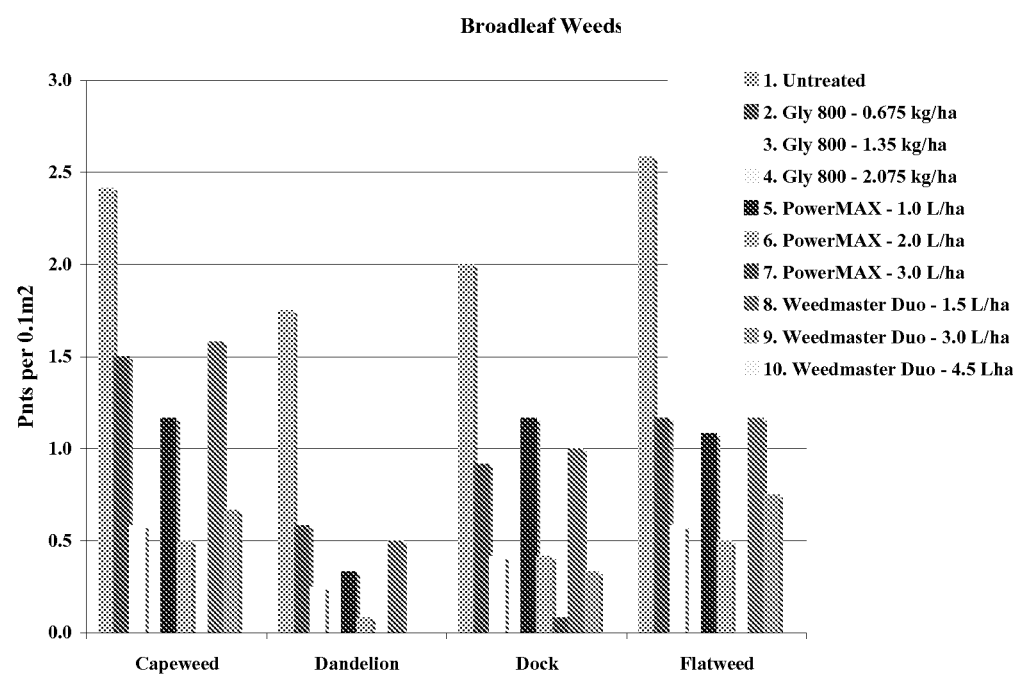
FIG. 2 illustrates broadleaf plant counts in a plot after treatment with formulations according to the present invention when compared to the commercially available formulations PowerMAX and Weedmaster Duo.

FIG. 2 illustrates broadleaf plant counts in a plot after treatment with formulations according to the present invention when compared to the control PowerMAX and Weedmaster Duo.

9.1. Trial Aims
1. To evaluate Gly 800 for knockdown of grasses and various broadleaf weeds.
2. To compare Gly 800 to the industry standards, Roundup PowerMAX and Weedmaster Duo.

9.2. Methods and Materials
9.2.1 Site Details
Site

| Site | Jenkins Orchard |
|---|---|

Soil

| Type | Loam | pH | 6.5 |
|---|---|---|---|
| Moisture | Fair | Drainage | Good |
| Tilth | Good | Organic Matter | Medium |
| Fertility | Good | | |

Trial

| Design | Randomised Complete Block Design | Plot Size | 1.0 m × 5 m | Replications | 4 |
|---|---|---|---|---|---|

Site History

| Chemicals Used* | Old Apple Orchard area - trees have been removed No chemicals used |
|---|---|
| Fertiliser Used* | Nil |

*21 Days prior and post trial application

9.2.2 Target Weeds

| Common Name | Scientific Name | Growth Stage | Plant Numbers/ Population |
|---|---|---|---|
| Couch | Cynodon dactylon | Vegetative | 30.8% |
| Kikuyu | Pennisetum clandestinum | Vegetative | 4.1% |
| Ryegrass Perennial | Lolium perenne | Vegetative | 11.8% |
| Paspalum | Paspalum dilatatum | Vegetative | 6.4/0.1 m$^2$ |
| Capeweed | Arctotheca calendula | Vegetative | 2.4/0.1 m$^2$ |
| Dandelion | Taraxacum officinale | Vegetative | 1.8/0.1 m$^2$ |
| Dock Curled | Rumex crispus | Vegetative | 2.0/0.1 m$^2$ |
| Flatweed | Hypochaeris radicata | Vegetative | 2.6/0.1 m$^2$ |
| Plantain | Plantago lanceolata | Vegetative | 2.4/0.1 m$^2$ |
| Soursob | Oxalis pes-caprae | Vegetative | 3.8/0.1 m$^2$ |
| Sub Clover | Trifolium subterranean | Vegetative | 4.1/0.1 m$^2$ |
| Creeping Speedwell | Veronica persica | Vegetative | 2.0/0.1 m$^2$ |

9.2.3 Application Details

Trial location and Plan    Jenkins Orchard, Knox

N ←

| 3 | 4 |
|---|---|
| 1 | 2 |

Rep 3                                                    Rep 4

| 5 | 4 | 1 | 6 | 3 | 9 | 8 | 7 | 10 | 2 | 5 | 3 | 4 | 1 | 9 | 2 | 7 | 10 | 8 | 6 |
|---|---|---|---|---|---|---|---|---|---|---|---|---|---|---|---|---|---|---|---|
| 1 | 2 | 3 | 4 | 5 | 7 | 6 | 8 | 9 | 10 | 7 | 1 | 9 | 3 | 6 | 10 | 8 | 2 | 5 | 4 |

Rep 1                                                    Rep 2

Water volume    123 L/ha    Situation    old apple orchard

Application Details

| Date | 29 Jul. 2008 |
|---|---|
| Time | 3:30-5:15 pm |
| Wind | calm |
| Temp | 12-14° C. |
| Humidity | 60% |
| Cloud Cover | 0% |
| Spray Order | 6, 5, 7, 9, 8, 10, 4, 3, 2 |

Trial was sprayed using a Hardi hand held boomspray, pressurised knapsack sprayer connected to a single Hardi 4110-12 flat fan nozzle. Flow rate per nozzle of 0.6 L/minute, with 2 L mixtures walking speed of 1.0 m/sec.

Comments on Mixing
  All products mixed easily in the water

9.2.4 Chemicals Used

| Code | Details | Formulation | Active Ingredient and Concentration |
|---|---|---|---|
| Gly 800 | | Granules | 800 g/kg |
| PowerMAX | Roundup Power Max Herbicide By Monsanto | Aqueous concentrate | 540 g/L glyphosate acid equivalent present as the potassium salt |
| Weedmaster Duo | Nufarm Weedmaster Duo Dual Salt Technology Herbicide J090338 Dec/07 | solution | 360 g/L glyphosate acid equivalent present as the isopropylamine and mono-ammonium salts |

9.2.5 Treatments
Treatments

| TTT No. | Product | Rate per ha | g gly ai (as acid equivalent) per hectare | Mixing Rate per 2 L |
|---|---|---|---|---|
| 1 | Untreated | — | — | — |
| 2 | Gly 800 | 0.675 kg | 540 | 11.0 g |
| 3 | Gly 800 | 1.350 kg | 1080 | 22.0 g |
| 4 | Gly 800 | 2.025 kg | 1620 | 32.9 g |
| 5 | PowerMAX | 1.0 L | 540 | 16.2 mL |
| 6 | PowerMAX | 2.0 L | 1080 | 32.5 mL |
| 7 | PowerMAX | 3.0 L | 1620 | 48.8 mL |
| 8 | Weedmaster Duo | 1.5 L | 540 | 24.4 mL |

-continued

| TTT No. | Product | Rate per ha | g gly ai (as acid equivalent) per hectare | Mixing Rate per 2 L |
|---|---|---|---|---|
| 9 | Weedmaster Duo | 3.0 L | 1080 | 48.8 mL |
| 10 | Weedmaster Duo | 4.5 L | 1620 | 73.2 mL |

9.2.6 Assessment Methods
Assessment Methods for Efficacy

| Assessment | Method |
|---|---|
| Efficacy | 1. Weed Phytotoxicity ratings<br>Scale 0 to 10 via visual assessment.<br>0 = No damage evident<br>1 = Negligible: discolouration, distortion, and/or stunting barely seen.<br>2 = Slight: discolouration, distortion, and/or stunting clearly seen.<br>3 = Moderate damage: moderate discolouration, marked distortions and/or stunting, recovery expected.<br>4 = Substantial damage: much discolouration, distortions and/or stunting, some damage probably irreversible.<br>5 = Majority of plants damaged, many irreversibly, some necrosis, discolouration and distortions severe.<br>6 = Nearly all plants damaged, most irreversibly, some plants killed (<40%), substantial necrosis and distortion.<br>7 = Severe: Substantial number of plants killed (40-60%), much necrosis and distortion.<br>8 = Very severe: Majority of plants killed (60-80%), remainder show much necrosis and wilting.<br>9 = Remaining live plants (<20%) mostly discoloured and distorted permanently or desiccated.<br>10 = Complete loss of plant (or) crop yield.<br>2. % Area Covered<br>At 31 days after treatment the grass weeds; couch, kikuyu and perennial ryegrass were assessed by determining the area of 3 × 0.1 m² quadrats per plot covered by the weed.<br>3. Weed Counts<br>At 31 days after treatment the broadleaf weeds and Paspalum were assessed by counting the weeds present in 3 × 0.1 m² quadrats per plot. |

9.2.7 Assessment & Assessment Timings

| Assessment Number | Days After Treatment | Assessment Type |
|---|---|---|
| 1 | 7 | Weed Phytotoxicity rating |
| 2 | 18 | Weed Phytotoxicity rating |
| 3 | 31 | Weed Phytotoxicity rating<br>% Area Covered - Grasses<br>Weed Counts |

9.2.8 Data Analysis
Weed Ratings

Plot ratings per plot were subject to a simple analysis of variance. Treatment means were separated using the Duncan's New Multiple Range Test with data not sharing common letters being significant at the 5% level.

Analyses were conducted both including and excluding the untreated plots.
Broadleaf Weed Counts Mean weeds counts per plot were subject to a simple analysis of variance. Treatment means were separated using the Duncan's New Multiple Range Test with data not sharing common letters being significant at the 5% level.
Grass % Coverage Mean percentage coverage per plot was converted to '% Reduction' and was subject to a simple analysis of variance. Treatment '% Reduction' were separated using the Duncan's New Multiple Range Test with data not sharing common letters being significant at the 9.3. Results
9.3.1 Efficacy—Ratings

TABLE 9.1

Weed Phytotoxicity Ratings

| | Assessment | | |
|---|---|---|---|
| | 1 | 2 | 3 |
| | | Date | |
| | 5-Aug-08 | 16-Aug-08 | 29-Aug-08 |
| | | DAT | |
| Treatments | 7 DAT | 18 DAT | 31 DAT |
| 1. Untreated | 0.0 | 0.0 | 0.0 |
| 2. Gly 800 - 0.675 kg/ha | 4.6 | 6.1 a | 8.1 a |
| 3. Gly 800 - 1.35 kg/ha | 4.8 | 7.6 b | 8.6 abc |
| 4. Gly 800 - 2.075 kg/ha | 4.8 | 8.3 b | 10.0 d |
| 5. PowerMAX - 1.0 L/ha | 4.8 | 6.3 a | 8.3 ab |
| 6. PowerMAX - 2.0 L/ha | 5.9 | 7.3 ab | 9.3 bcd |
| 7. PowerMAX - 3.0 L/ha | 5.9 | 7.0 ab | 9.4 cd |
| 8. Weedmaster Duo - 1.5 L/ha | 4.8 | 7.0 ab | 9.0 abcd |
| 9. Weedmaster Duo - 3.0 L/ha | 5.3 | 7.4 ab | 9.5 cd |
| 10. Weedmaster Duo - 4.5 L/ha | 6.0 | 8.3 b | 9.9 d |
| LSD (p < 0.05)# | NS | 1.284 | 1.040 | analyses excluding the untreated plots.

9.3.2 Efficacy—Grass Weeds

TABLE 9.2

Grass Weeds - % Coverage/Plant Numbers

| | Weed | | | |
|---|---|---|---|---|
| | Couch | Kikuyu | Ryegrass | *Paspalum* |
| | | Assessment | | |
| | % Coverage | | | Count |
| | Date 29-Aug-08 | | | |
| Treatments | DAT 31 DAT | | | |
| 1. Untreated | 30.8 | 4.1 | 11.8 | 6.4 |
| 2. Gly 800 - 0.675 kg/ha | 7.3 | 2.1 | 4.7 | 2.8 |
| 3. Gly 800 - 1.35 kg/ha | 3.3 | 0.8 | 1.0 | 1.1 |
| 4. Gly 800 - 2.075 kg/ha | 0.0 | 0.0 | 0.0 | 0.0 |
| 5. PowerMAX - 1.0 L/ha | 7.5 | 1.3 | 3.3 | 3.2 |
| 6. PowerMAX - 2.0 L/ha | 4.0 | 1.5 | 1.5 | 1.8 |
| 7. PowerMAX - 3.0 L/ha | 0.1 | 0.1 | 0.1 | 0.0 |
| 8. Weedmaster Duo - 1.5 L/ha | 6.8 | 3.1 | 2.6 | 4.0 |
| 9. Weedmaster Duo - 3.0 L/ha | 5.2 | 2.1 | 0.8 | 1.0 |
| 10. Weedmaster Duo - 4.5 L/ha | 0.2 | 0.2 | 0.0 | 0.0c |

TABLE 9.3

Grass Weeds - % Reduction in Coverage

| | Weed | | |
|---|---|---|---|
| | Couch | Kikuyu | Ryegrass |
| | | Assessment | |
| | | % Coverage | |
| | | Date 29 Aug 2008 | |
| Treatments | | DAT 31 DAT | |
| 2. Gly 800 - 0.675 kg/ha | 73.9 b | 46.5 cd | 53.6 d |
| 3. Gly 800 - 1.35 kg/ha | 87.7 ab | 81.0 ab | 89.9 ab |
| 4. Gly 800 - 2.075 kg/ha | 100.0 a | 100.0 a | 100.0 a |

TABLE 9.3-continued

Grass Weeds - % Reduction in Coverage

| | Weed | | |
|---|---|---|---|
| | Couch | Kikuyu | Ryegrass |
| | | Assessment | |
| | | % Coverage | |
| | | Date 29 Aug 2008 | |
| Treatments | | DAT 31 DAT | |
| 5. PowerMAX - 1.0 L/ha | 69.4 b | 67.2 bc | 65.7 cd |
| 6. PowerMAX - 2.0 L/ha | 86.7 ab | 64.9 bc | 85.7 abc |
| 7. PowerMAX - 3.0 L/ha | 99.8 a | 97.9 a | 99.6 bcd |
| 8. Weedmaster Duo - 1.5 L/ha | 74.4 b | 25 d | 72.2 bcd |
| 9. Weedmaster Duo - 3.0 L/ha | 82.4 ab | 53.7 c | 91.4 ab |
| 10. Weedmaster Duo - 4.5 L/ha | 99.3 a | 94.4 a | 100.0 a |
| LSD (p < 0.05) | 21.0 | 26.8 | 22.6 |

TABLE 9.4

Grass Weed - *Paspalum* - % Reduction in Plant Numbers
Weed *Paspalum*
Assessment Count
Date 29-Aug-08
DAT 31 DAT

| Treatments | |
|---|---|
| 2. Gly 800 - 0.675 kg/ha | 55.0 cd |
| 3. Gly 800 - 1.35 kg/ha | 81.3 ab |
| 4. Gly 800 - 2.075 kg/ha | 100.0 a |
| 5. PowerMAX - 1.0 L/ha | 48.9 d |
| 6. PowerMAX - 2.0 L/ha | 72.6 bc |
| 7. PowerMAX - 3.0 L/ha | 100.0 a |
| 8. Weedmaster Duo - 1.5 L/ha | 35.5 d |
| 9. Weedmaster Duo - 3.0 L/ha | 83.5 ab |
| 10. Weedmaster Duo - 4.5 L/ha | 100.0 a |
| LSD (p < 0.05) | 22.5 |

9.3.3 Efficacy—Broadleaf Weeds

TABLE 9.5

Broadleaf Weeds - Plant Numbers

| | Weed | | | |
|---|---|---|---|---|
| | Clover | Plantain | Soursob | Speedwell |
| | | Assessment | | |
| | | Plant Numbers | | |
| | | Date 29-Aug-08 | | |
| Treatments | | DAT 31 DAT | | |
| 1. Untreated | 4.1 a | 2.4 a | 3.8 a | 2.0 a |
| 2. Gly 800 - 0.675 kg/ha | 1.8 b | 1.5 b | 1.6 b | 1.1 bc |
| 3. Gly 800 - 1.35 kg/ha | 0.7 cd | 0.7 cd | 0.6 cd | 0.7 cd |
| 4. Gly 800 - 2.075 kg/ha | 0.0 d | 0.0 d | 0.0 d | 0.0 e |
| 5. PowerMAX - 1.0 L/ha | 1.3 bc | 1.4 b | 1.4 b | 1.0 bc |
| 6. PowerMAX - 2.0 L/ha | 0.8 cd | 0.2 d | 0.4 cd | 1.2 bc |
| 7. PowerMAX - 3.0 L/ha | 0.0 d | 0.0 d | 0.0 d | 0.1 de |
| 8. Weedmaster Duo - 1.5 L/ha | 1.4 bc | 1.1 bc | 1.4 b | 1.3 b |
| 9. Weedmaster Duo - 3.0 L/ha | 1.2 c | 0.6 cd | 0.7 c | 1.1 bc |
| 10. Weedmaster Duo - 4.5 L/ha | 0.3 d | 0.0 d | 0.1 cd | 0.0 e |
| LSD (p < 0.05) | 0.761 | 0.720 | 0.594 | 0.470 |

TABLE 9.6

Broadleaf Weeds - Plant Numbers

| | Weed | | | |
|---|---|---|---|---|
| | Capeweed | Dandelion | Dock | Flatweed |
| | | Assessment | | |
| | | Plant Numbers | | |
| | | Date 29-Aug-08 | | |
| Treatments | | DAT 31 DAT | | |
| 1. Untreated | 2.4 a | 1.8 a | 2.0 a | 2.6 a |
| 2. Gly 800 - 0.675 kg/ha | 1.5 b | 0.6 b | 0.9 bc | 1.2 b |
| 3. Gly 800 - 1.35 kg/ha | 0.6 cde | 0.3 bc | 0.4 cd | 0.6 c |
| 4. Gly 800 - 2.075 kg/ha | 0.0 e | 0.0 c | 0.0 d | 0.0 d |
| 5. PowerMAX - 1.0 L/ha | 1.2 bc | 0.3 bc | 1.2 b | 1.1 b |
| 6. PowerMAX - 2.0 L/ha | 0.5 de | 0.1 bc | 0.4 cd | 0.5 c |
| 7. PowerMAX - 3.0 L/ha | 0.0 e | 0.0 c | 0.1 d | 0.0 d |
| 8. Weedmaster Duo -1.5 L/ha | 1.6 b | 0.5 bc | 1.0 b | 1.2 b |
| 9. Weedmaster Duo - 3.0 L/ha | 0.7 cd | 0.0 c | 0.3 d | 0.8 bc |
| 10. Weedmaster Duo - 4.5 L/ha | 0.0 e | 0.0 c | 0.0 d | 0.0 d |
| LSD (p < 0.05) | 0.652 | 0.538 | 0.581 | 0.491 |

9.4. Discussion

9.4.1 Whole Plot Ratings

Whole plot weed phytotoxicity ratings were made at 9, 17 and 31 days after treatment (DAT). At each assessment all treatments showed significant weed phytotoxicity compared to the untreated control, Table 1 (LSD analyses in Appendix 2).

At 9 DAT there was no significant difference between any treatments. At 18 DAT only Gly 800 at 1.35 kg/ha & 2.75 kg/ha and Weedmaster Duo at 4.5 L/ha were statistically superior to Gly 800 at 0.675 kg/ha and PowerMAX at 1.0 L/ha, Table 1.

At 31 DAT only Gly 800 at 2.075 kg/ha achieved 10, although it was not statistically different to PowerMAX at 2.0 & 3.0 L/ha and Weedmaster Duo at 1.5, 3.0 & 4.5 L/ha, Table 1.

The mean rating, across all treatments at each assessment time increased from 5.2 to 7.2, then to 9.1, at the last assessment time, showing increased phytotoxicity over time.

There was an increase in phytotoxicity rating associated with increasing rate, Table 7.

TABLE 9.7

Effect of Rate on Weed Phytotoxicity (All Assessments Timings)

| | Rate of Glyphosate | | |
|---|---|---|---|
| Treatment | Low | Medium | High |
| Gly 800 | 18.9 | 21.0 | 23.0 |
| PowerMAX | 19.3 | 22.4 | 22.3 |
| Weedmaster Duo | 20.8 | 22.1 | 24.1 |

At each assessment time there was no significant difference in the weed rating between either product when applied at the same rate of glyphosate active per hectare, Table 1. In summary, all treatments achieved significant levels of weed phytotoxicity with increasing time and increasing the rate of glyphosate active increasing the level of phytotoxicity.

There was no significant difference between the three products in respect of whole plot ratings when applying the same quantity of glyphosate.

9.4.2 Efficacy—Grass Weeds

Couch

The untreated plots were assessed to have an average 30.8% coverage of couch, Table 2, this ranged from 18.3% to 43%.

All treatments significantly reduced the amount of couch present, with Gly 800 obtaining 100% reduction, Table 3 & 8.

TABLE 9.8

Couch - % Reduction in Coverage (All Assessments Timings)

| Treatment | Rate of Glyphosate | | |
|---|---|---|---|
| | Low | Medium | High |
| Gly 800 | 73.9 | 87.7 | 100.0 |
| PowerMAX | 69.4 | 86.7 | 99.8 |
| Weedmaster Duo | 74.4 | 82.4 | 99.3 |

There was no significant difference in the reduction of couch between the three products when applying the same amount of glyphosate per hectare, Table 9.3.

Kikuyu

The untreated plots were assessed to have an average of 4.1% coverage of Kikuyu, Table 2, this ranged from 3.0 to 5.7%.

All treatments significantly reduced the amount of couch present, there was a good dose response, with Gly 800 at the high rate either and Weedmaster Duo both achieved 100% reduction, Tables 9.3 & 9.9.

TABLE 9.9

Kikuyu - % Reduction in Coverage (All Assessments Timings)

| Treatment | Rate of Glyphosate | | |
|---|---|---|---|
| | Low | Medium | High |
| Gly 800 | 46.5 | 81.0 | 100 |
| PowerMAX | 67.2 | 64.9 | 97.9 |
| Weedmaster Duo | 25.0 | 53.7 | 94.4 |

There was no significant difference in the reduction of Kikuyu between the three products when applying the same amount of glyphosate per hectare, Table 9.3.

Ryegrass

The untreated plots were assessed to have an average of 11.8% coverage of couch, Table 9.2, this ranged from 7.0 to 23.7%.

All treatments significantly reduced the amount of couch present, there was a good dose response, with Gly 800 and Weedmaster Duo giving 100% reduction, with PowerMAX achieving 99.6% reduction at the highest rate, Table 9.3 & 9.10.

TABLE 9.10

Ryegrass - % Reduction in Coverage (All Assessments Timings)

| Treatment | Rate of Glyphosate | | |
|---|---|---|---|
| | Low | Medium | High |
| Gly 800 | 53.6 | 89.9 | 100 |
| PowerMAX | 65.7 | 85.7 | 99.6 |
| Weedmaster Duo | 72.2 | 91.4 | 100 |

There was no significant difference in the reduction of couch coverage between the three products when applying the same amount of glyphosate per hectare, Table 9.2.

Paspalum

The levels of *paspalum* were low with untreated plots having only an average of 6.4 plants per 0.1 $m^2$, Table 2, this ranged from 4.0 to 8.0.

All treatments significantly reduced the amount of *paspalum* present while a strong dose response was evident. The lowest levels of glyphosate achieved control levels ranging from 35 to 55%, while at the highest rate all three products obtained 100% control, Table 9.4 & 9.11.

TABLE 9.11

Paspalum - % Reduction in Plant Numbers (All Assessments Timings)

| Treatment | Rate of Glyphosate | | |
|---|---|---|---|
| | Low | Medium | High |
| Gly 800 | 55.0 | 81.3 | 100 |
| PowerMAX | 48.9 | 72.6 | 100 |
| Weedmaster Duo | 35.5 | 83.5 | 100 |

There was no significant difference in the reduction of *paspalum* between the three products when applying the same amount of glyphosate per hectare, Table 9.4.

9.4.3 Efficacy—Broadleaf Weeds

Counts of broadleaf present were made at 31 days after treatment (DAT) and all treatments showed significant effect on the various species of broadleaf weeds present, Tables 9.5 & 9.6.

The level of each broadleaf weed present were low to medium, with Clover and Soursob being the most numerous with average numbers of 4.1 & 3.8 plants per 0.1 $m^2$, with the other 6 weeds present ranging from 1.8 to 2.6 plants per 0.1 $m^2$.

All weeds showed significant response to the increase in glyphosate rate, Table 9.12, when all broadleaf weeds present were added per treatment.

TABLE 9.12

Broadleaf Weeds - Numbers Present 31DAT (total across all species)

| Treatment | Rate of Glyphosate | | |
|---|---|---|---|
| | Low | Medium | High |
| Gly 800 | 10.2 | 4.4 | 0.0 |
| PowerMAX | 8.8 | 4.1 | 0.2 |
| Weedmaster Duo | 9.5 | 5.3 | 0.3 |

At the highest rate of glyphosate Gly 800 achieved 100% control of all broadleaf weeds present, with PowerMAX obtaining 100% control of Clover, Plantain, Soursob, Capeweed, Dandelion and Flatweed, while Weedmaster Duo gave 100% control of Plantain, Speedwell, Capeweed, Dandelion Dock and Flatweed.

There was no significant difference in control of any of the broadleaf weeds when Gly 800, PowerMAX or Weedmaster Duo were applied at the same rate of glyphosate per hectare, Tables 5 & 6.

9.4. Conclusions

1. Gly 800 provided effective control of a range of grass and broadleaf weeds present in this trial.
2. Gly 800 achieved equivalent levels of weed control to the industry standards, Roundup PowerMAX and Weedmaster Duo, when applied at the same rate of glyphosate It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

Example 10

The following formulations were used in agronomic studies to assess the bioefficacy relative to commercial standards. Each formulation in the table below comprises a glyphosate acid/monoammonium glyphosate mixture.

The table below lists formulation inputs. In each case, these inputs were granulated and dried prior to use, and the final dry weight was 1000 parts.

| 800 g/kg glyphosate acid equivalent - ammonium salt | parts | Used In Agronomy Trial |
|---|---|---|
| Glyphosate acid (98% w/w) | 223 | No. A - ARG, this is example 11 |
| Mono-NH4 glyphosate | 653 | No. A - WR, this is example 12 |
| Cocoamidopropylbetaine (56% solution) | 217.5 | No. B - this is example 13 |
| water | 502.2 | |
| wet mass | 1595.7 | |
| Glyphosate acid (98% w/w) | 223 | No. A - ARG - this is example 11 |
| Mono-NH4 glyphosate | 653 | No. A - WR - this is example 12 |
| Cocobetaine (56% solution) | 217.5 | No. B - this is example 13 |
| water | 502.2 | |
| wet mass | 1595.7 | |
| Glyphosate acid (98% w/w) | 223 | |
| Mono-NH4 glyphosate | 653 | No. B - this is example 13 |
| Amine oxide | 217.5 | |
| water | 502.2 | |
| wet mass | 1595.7 | |
| Glyphosate acid (98% w/w) | 223 | |
| Mono-NH4 glyphosate | 653 | No. B - this is example 13 |
| Ethoxylated tallow amine | 124 | |
| water | 500 | |
| wet mass | 1500 | |
| Glyphosate acid (98% w/w) | 223 | |
| Mono-NH4 glyphosate | 653 | No. B - this is example 13 |
| Alykl diamine alkoxylate | 124 | |
| water | 450 | |
| wet mass | 1450 | |

Trial A-ARG relates to formulations according to the present invention comprising (i) cocoamidopropylbetaine (CAPB) and (ii) cocobetaine (CB) surfactants tested with annual ryegrass. Roundup Biactive® SL and Macphersons Bi Dri 700SG were the commercial standards.

Trial A-WR relates to formulations according to the present invention comprising (i) cocoamidopropylbetaine (CAPB) and (ii) cocobetaine (CB) surfactants tested with wild radish. Roundup Biactive® SL and Macphersons Bi Dri 700SG were the commercial standards.

Trial B relates to formulations according to the present invention comprising (i) cocoamidopropylbetaine (CAPB), (ii) cocobetaine (CB), (iii) cocoamineoxide (AO), (iv) ethoxylated tallowamine (15EOs) (TA), and (v) alkyldiamine alkoxylate (ADA) tested with annual rye grass.

The below table describes formulations which comprise a mixture of glyphosate acid and glyphosate monopotassium salt. After addition of the components, some water was generated by acid-base neutralisation and the wet material was extruded and subsequently dried. In all cases, the dried weight was 1000 parts.

| 720 g/kg glyphosate acid equivalent | parts | Used In Agronomy Trial |
|---|---|---|
| Glyphosate acid (98% w/w) | 734.7 | No. B/K+ - see example 14 |
| K+ glyphosate | 193.5 | |
| Cocoamidopropylbetaine (56% solution) | 228.6 | |
| water | | |
| wet mass | 1156.8 | |
| Glyphosate acid (98% w/w) | 734.7 | No. B/K+ - see example 14 |
| KOH (90% pellets) | 193.5 | |
| Cocobetaine (56% solution) | 228.6 | |
| water | | |
| wet mass | 1156.8 | |
| Glyphosate acid (98% w/w) | 734.7 | No. B/K+ - see example 14 |
| KOH (90% pellets) | 193.5 | |
| Amine oxide | 228.6 | |
| water | | |
| wet mass | 1156.8 | |
| Glyphosate acid (98% w/w) | 734.7 | No. B/K+ - see example 14 |
| KOH (90% pellets) | 193.5 | |
| Ethoxylated tallow amine | 128.6 | |
| water | | |
| wet mass | 1056.8 | |
| Glyphosate acid (98% w/w) | 734.7 | No. B/K+ - see example 14 |
| KOH (90% pellets) | 193.5 | |
| Alykl diamine alkoxylate | 128.6 | |
| water | | |
| wet mass | 1056.8 | |

The Examples below relate to formulations according to the present invention comprising (i) cocoamidopropylbetaine (CAPB), (ii) cocobetaine (CB), (iii) cocoamineoxide (AO), (iv) ethoxylated tallowamine (15EOs) (TA), and (v) alkyldiamine alkoxylate (ADA) tested with annual rye grass.

Example 11

Efficacy of Two Variants of Glyphosate 800SG (Cocobetaine or Cocoamidobetaine) and Two Commercial Standards on Annual Ryegrass (Trial No A-ARG)

Introduction

In this trial the efficacy of two variants of glyphosate 800SG (one made with a cocobetaine surfactant and one with a cocoamidopropylbetaine) were compared with two commercial standards (Roundup Biactive Soluble Liquid and Macphersons 700 g/kg SG). The trial was undertaken in pots using annual ryegrass as the test species at the Agricultural and Food Precinct in Werribee, Victoria, Australia.

Materials and Methods

Plant Propagation

Annual ryegrass (*Lolium rigidum*) seeds (5/pot) were sown 1 Mar. 2008 to a depth of 10 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 20 days prior to spray application to more closely simulate field conditions and toughen up plants. After the application of herbicides the pots were returned to the greenhouse for an additional 14 days before plants were harvested for fresh weight.

Herbicide and Spray Mix

There were two formulations of partially neutralized glyphosate 800SG, one contained a cocobetaine (CB) as the surfactant while the other contained a cocoamidopropyl betaines (CAPB).

Roundup Biactive® SL and Macphersons Bi Dri 700SG were the commercial standards.

The annual ryegrass was at the early tillering stage (2 tillers) when sprayed with the herbicide treatments.

Herbicide formulations were applied using an enclosed laboratory track-sprayer fitted with three 110° flat fan nozzles ("Teejet"® XR11001-VS) spaced at 50 cm intervals across the boom. The boom moved along a fixed track at 6 km h−1, sprayed at a water volume of 64 L/ha with a pressure of 200 kPa.

There were eight replicates for each treatment.

The products were added at the required rates directly to the water in the spray canister to give a total spray weight of 1,300 g (Table 11.1, Table 11.2, Table 11.3).

TABLE 11.1

Mixing ratios of Roundup Biactive and water for a spray volume of 64 L/ha.

| Glyphosate g acid/ha | Biactive g acid/L | Biactive ml/ha | Biactive ml/1.3 L | Water ml/canister |
|---|---|---|---|---|
| 45 | 360 | 125 | 2.45 | 1297.5 |
| 90 | 360 | 250 | 5.08 | 1294.9 |
| 180 | 360 | 500 | 10.16 | 1289.8 |
| 360 | 360 | 1000 | 20.32 | 1279.7 |
| 450 | 360 | 1250 | 25.39 | 1274.6 |

TABLE 11.2

Mixing Ratios Macphersons Bi Dri 700SG (Bi Dri)

| Glyphosate g acid/ha | Bi Dri. g acid/kg | Bi Dri. g/ha | Bi Dri g/1.3 L | Water ml/canister |
|---|---|---|---|---|
| 45 | 700 | 64.3 | 1.3 | 1298.7 |
| 90 | 700 | 129 | 2.6 | 1297.4 |
| 180 | 700 | 257 | 5.2 | 1294.8 |
| 360 | 700 | 514 | 10.5 | 1289.5 |
| 450 | 700 | 643 | 13.0 | 1287.0 |

TABLE 11.3

Mixing Ratios for both Glyphosate 800SG formulations.

| Glyphosate g acid/ha | 800SG g acid/kg | 800SG g/ha | 800SG g/1.3 L | Water ml/canister |
|---|---|---|---|---|
| 45 | 800 | 56.3 | 1.1 | 1298.9 |
| 90 | 800 | 112.5 | 2.3 | 1297.7 |
| 180 | 800 | 225 | 4.6 | 1295.4 |
| 360 | 800 | 500 | 9.2 | 1290.8 |
| 450 | 800 | 563 | 11.4 | 1288.6 |

Assessment

Seedlings were harvested 14 days after spray application by cutting foliage off at the base immediately prior to weighing on an "AND FX" 300 electronic balance (range 0-300 g).

Statistic Analysis

Data was analysed using a factorial design with two factors, glyphosate formulation (Formulation) and spray application rate (Rate). 95% least significant differences (LSD) were calculated for the mean of each treatment.

Results

Analysis of Variance

There was no significant effect of Formulation, a highly significant effect of Rate but no significant interaction (Table 11.4).

TABLE 11.4

Analysis of variance of the fresh weight of annual ryegrass treated with five rates of three different glyphosate formulations.

| Factor | FPr | LSD (g/plant) |
|---|---|---|
| Formulation | 0.10 | NS |
| Rate | <0.001 | 0.51 |
| Form × Rate | 0.90 | NS |

Formulation

There was no significant difference in the efficacy of the four formulations (Table 11.5). This indicates that the four formulations all had a similar efficacy.

Rate

As would be expected there was a significant decline in fresh weight with each increase in application rate (Table 11.5).

TABLE 11.5

Fresh weight (g/plant) of annual ryegrass plants harvested after treatment with four glyphosate formulations. Mean Rate data in the same column or Mean Formulation data in the same row that are followed by the same letter are not significantly different ($P < 0.05$).

| Glyphosate rate g acid/ha | Glyphosate 800SG CB | Glyphosate 800SG CAPB | Bi Dri. | Biactive | Rate Mean |
|---|---|---|---|---|---|
| 0 |  |  | 9.5 |  |  |
| 45 | 8.3 | 8.5 | 8.8 | 8.8 | 8.6 e |
| 90 | 6.8 | 7.0 | 6.6 | 6.3 | 6.6 d |
| 180 | 3.9 | 4.4 | 3.9 | 3.7 | 3.8 c |
| 360 | 1.7 | 1.7 | 1.6 | 1.6 | 1.7 b |
| 450 | 0.5 | 0.6 | 0.5 | 04 | 0.5 a |
| Formulation Mean (not including the 0 gai/ha) | 4.3 | 4.4 | 4.3 | 4.2 |  |

Conclusion

Figure 3:
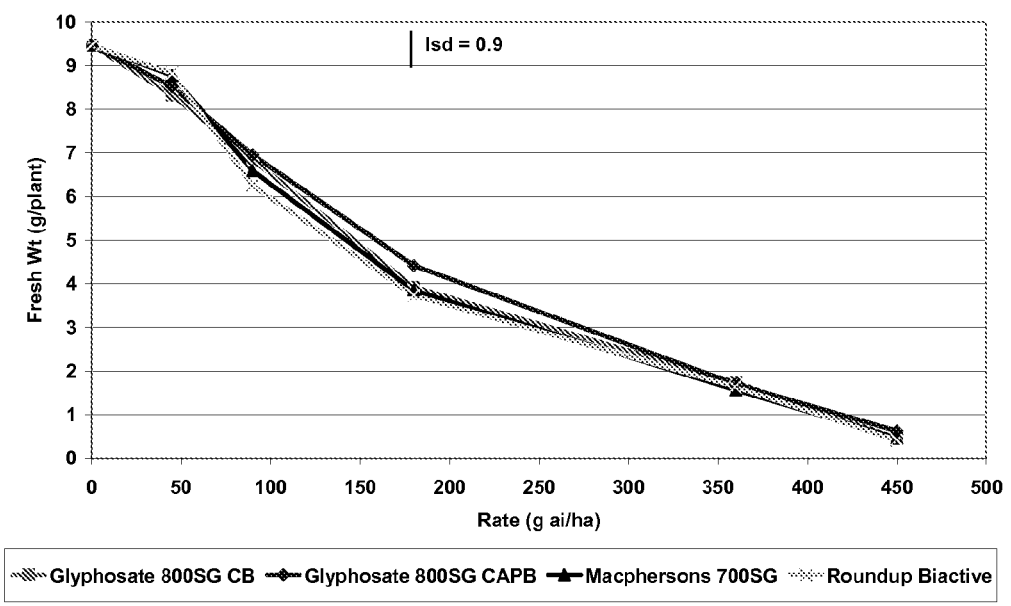
FIG. 3 illustrates fresh weight of annual ryegrass treated with formulations according to the present invention (glyphosphate 800 SG containing a cocobetaine (CB) or a cocoamidopropyl betaine (CAPB)) and two commercially available formulations (Roundup Biactive (RUP Biactive) 360SL and Macphersons Bi Dri (700 G/KG SG))

Under the conditions tested the formulations were bioequivalent for their efficacy on annual ryegrass (FIG. 3). The formulations of partially neutralized glyphosate made up with cocobetaine or cocoamidobetaine surfactants had a similar efficacy to the commercials standards Roundup Biactive and Macphersons Bi Dri.

Example 12

Efficacy of Two Variants of Glyphosate 800SG (Cocobetaine or Cocoamidobetaine) and Two Commercial Standards on Wild Radish (Trial No. A-WR)

Introduction

In this trial the efficacy of two variants of glyphosate 800SG (one made with a cocobetaine surfactant and one with a cocoamidopropylbetaine) were compared with two commercial standards (Roundup Biactive Soluble Liquid and Macphersons 700 g/kg SG). The trial was undertaken in pots using wild radish as the test species at the Agricultural and Food Precinct in Werribee, Victoria, Australia.

Materials and Methods

Plant Propagation

Wild radish (*Raphanus raphanistrum*) seeds (3/pot) were sown to a depth of 3 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 21 days prior to spray application to more closely simulate field conditions (and to harden up plants). After the application of herbicides the pots were returned to the greenhouse for an additional 14 days before plants were assessed for fresh weight.

Herbicide and Spray Mix

There were two formulations of partially neutralized glyphosate 800SG, one contained a cocobetaine (CB) as the surfactant while the other contained a cocoamidopropyl betaines (CAPB).

Roundup Biactive® SL and Macphersons Bi Dri 700SG were the commercial standards.

The wild radish plants were in the rosette stage with 5-7 leaves when sprayed with the herbicide.

Herbicide formulations were applied using an enclosed laboratory track-sprayer fitted with three 110° flat fan nozzles ("Teejet"® XR11001-VS) spaced at 50 cm intervals across the boom. The boom moved along a fixed track at 6 km h−1, sprayed at a water volume of 64 L/ha with a pressure of 200 kPa.

There were eight replicates for each treatment.

The products were added at the required rates directly to the water in the spray canister to give a total spray weight of 1,300 g (Table 12.1, Table 12.2, Table 12.3).

TABLE 12.1

Mixing ratios of Roundup Biactive and water.

| Glyphosate g acid/ha | Glyphosate g acid/L | Glyphosate g acid/1.3 L | Biactive g acid/L | Biactive ml/1.3 L | Water ml/canister |
|---|---|---|---|---|---|
| 45 | 0.70 | 0.91 | 360 | 2.54 | 1297.5 |
| 90 | 1.41 | 1.83 | 360 | 5.08 | 1294.9 |
| 180 | 2.81 | 3.65 | 360 | 10.16 | 1289.8 |
| 360 | 5.63 | 7.32 | 360 | 20.32 | 1279.7 |
| 450 | 7.03 | 9.1 | 360 | 25.39 | 1274.6 |

TABLE 12.2

Mixing Ratios Macphersons Bi Dri 700SG

| Glyphosate g acid/ha | Glyphosate g acid/L | Glyphosate g acid/1.3 L | Bi Dri. g acid/L | Bi Dri g/1.3 L | Water ml/canister |
|---|---|---|---|---|---|
| 45 | 0.70 | 0.91 | 700 | 1.3 | 1298.7 |
| 90 | 1.41 | 1.83 | 700 | 2.6 | 1297.4 |
| 180 | 2.81 | 3.65 | 700 | 5.2 | 1294.8 |
| 360 | 5.63 | 7.32 | 700 | 10.5 | 1289.5 |
| 450 | 7.03 | 9.1 | 700 | 13.0 | 1287.0 |

TABLE 12.3

Mixing Ratios for both Glyphosate 800SG formulations

| Glyphosate g acid/ha | Glyphosate g acid/L | Glyphosate g acid/1.3 L | 800SG g acid/L | 800SG g/1.3 L | Water ml/canister |
|---|---|---|---|---|---|
| 45 | 0.70 | 0.91 | 800 | 1.1 | 1298.9 |
| 90 | 1.41 | 1.83 | 800 | 2.3 | 1297.7 |
| 180 | 2.81 | 3.65 | 800 | 4.6 | 1295.4 |
| 360 | 5.63 | 7.32 | 800 | 9.2 | 1290.8 |
| 450 | 7.03 | 9.1 | 800 | 11.4 | 1288.6 |

Assessment

Seedlings were harvested 14 d after spray application by cutting foliage off at the base immediately prior to weighing on an "AND FX" 300 electronic balance (range 0-300 g).

Statistic Analysis

Data was analysed using a factorial design with two factors, glyphosate formulation (Formulation) and spray application rate (Rate). 95% least significant differences (LSD) were calculated for the mean of each treatment.

Results

Analysis of Variance

There was no significant effect of formulation, a highly significant effect of Rate but no significant interaction (Table 12.4).

TABLE 12.4

Analysis of variance of the fresh weight of wild radish treated with six rates of three different glyphosate formulations.

| Factor | FPr | LSD (g/plant) |
|---|---|---|
| Formulation | 0.91 | NS |
| Rate | <0.001 | 0.61 |
| Form × Rate | 0.41 | NS |

Formulation

There was no significant difference in the efficacy of the four formulations (Table 12.5). This indicates that the four formulations all had a similar efficacy.

Rate

As would be expected there was a significant decline in fresh weight with each increase in application rate (Table 12.5).

TABLE 12.5

Fresh weight (g/plant) of wild radish harvested after treatment with four glyphosate formulations. Mean Rate data in the same column or Mean Formulation data in the same row that are followed by the same letter are not significantly different (P < 0.05).

| Glyphosate rate g acid/ha | Glyphosate 800SG CB | Glyphosate 800SG CAPB | Bi Dri. | RUP Biactive | Rate Mean |
|---|---|---|---|---|---|
| 0 | | 12.5 | | | 12.5 |
| 45 | 12.6 | 11.5 | 12.1 | 11.8 | 12.1 d |
| 90 | 9.2 | 8.8 | 8.9 | 8.9 | 9.0 c |
| 180 | 6.6 | 6.8 | 6.8 | 6.7 | 6.7 b |
| 360 | 3.8 | 4.1 | 4.4 | 4.9 | 4.4 a |
| 450 | 3.8 | 3.8 | 3.7 | 4.1 | 3.9 a |
| Formulation Mean (not including the 0 g ai/ha) | 7.2 | 7.0 | 7.1 | 7.3 | |

Conclusion

Figure 4:
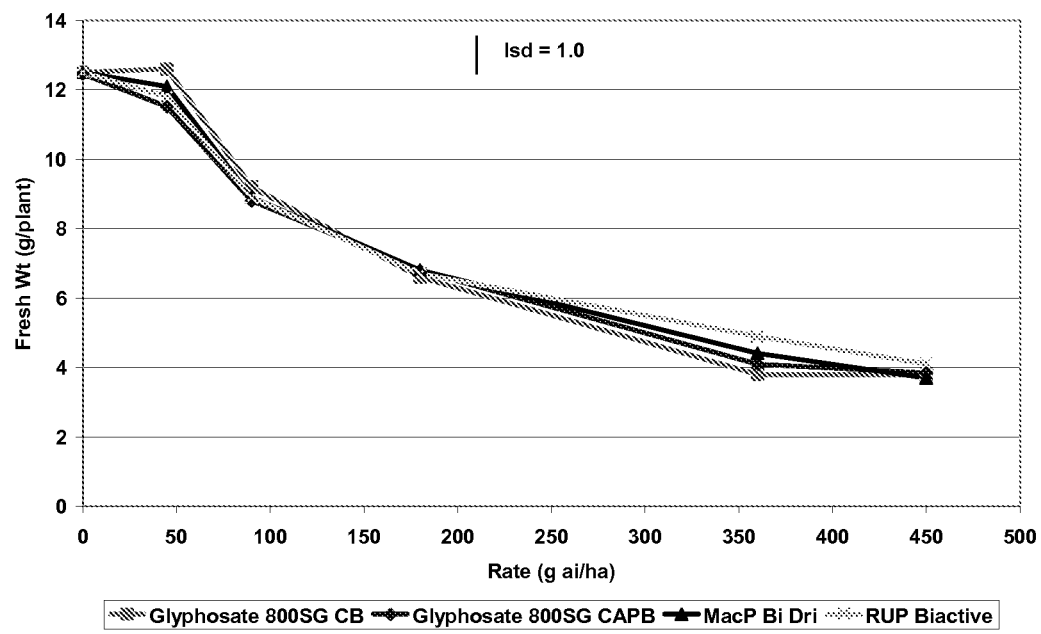
FIG. 4 illustrates fresh weight of wild radish treated with formulations according to the present invention (glyphosphate 800 SG containing a cocobetaine (CB) or a cocoamidopropyl betaine (CAPB)) and two commercially available formulations (Roundup Biactive (RUP Biactive) 360SL and Macphersons Bi Dri (700 G/KG SG)).

Under the conditions tested the formulations were bioequivalent for their efficacy on wild radish (FIG. 4). The formulations of partially neutralized glyphosate made up with cocobetaine or cocoamidobetaine surfactants had a similar efficacy to the commercials standards Roundup Biactive and Macphersons Bi Dri.

Example 13

Efficacy of Glyphosate 800SG on Annual Ryegrass (Trial No. B)

Introduction

The present inventors evaluated the efficacy of partially neutralized glyphosate formulations in a pot trial. The project was carried out at Agricultural and Food Precinct in Werribee, Victoria.

Materials and Methods
Plant Propagation

Annual ryegrass (*Lolium rigidum*) seeds (5/pot) were sown 1 Mar. 2008 to a depth of 10 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 20 days prior to spray application to more closely simulate field conditions and toughen up plants. After the application of herbicides the pots were returned to the greenhouse for an additional 14 days before plants were harvested for fresh weight.

Formulations

Five granule formulations were made using ammonium glyphosate salt plus acid to a concentration of 800 g acid equivalent (Table 13.1). The efficacy of these formulations was compared with that of a commercial standard granule formulation Macphersons 700Bi Dri (Bi Dri). The surfactant used in the Bi Dri formulation was a cocobetaine.

TABLE 13.1

Formulations used in trial

| Code | Glyphosate (g/kg) | In product Surfactant System |
| --- | --- | --- |
| 800NH4-CB | 800 as $NH_4^+$ salt + acid | Cocobetaine |
| 800NH4-CAPB | | Cocoamidopropylbetaine |
| 800NH4-TA | | Ethoxylated tallow amine |
| 800NH4-AO | | Amine oxide |
| 800NH4-ADA | | Alkyl diamine alkoxylate |
| Bi Dri | 700 as $NH_4^+$ salt | Cocobetaine |

Herbicide and Spray Mix

The formulations were added at the required rates directly to the water in the spray canister to give a total spray weight of 1,300 g (Table 13.2, Table 13.3).

TABLE 13.2

Mixing Ratios Macphersons Bi Dri 700SG

| Glyphosate g acid/ha | Glyphosate g acid/L | Glyphosate g acid/1.3 L | Bi Dri. g acid/kg | Bi Dri g/1.3 L | Water ml/canister |
| --- | --- | --- | --- | --- | --- |
| 45 | 0.70 | 0.91 | 700 | 1.3 | 1298.7 |
| 90 | 1.41 | 1.83 | 700 | 2.6 | 1297.4 |
| 180 | 2.81 | 3.65 | 700 | 5.2 | 1294.8 |
| 360 | 5.63 | 7.32 | 700 | 10.5 | 1289.5 |
| 450 | 7.03 | 9.1 | 700 | 13.0 | 1287.0 |

TABLE 13.3

Mixing Ratios for glyphosate 800SG formulations.

| Glyphosate g acid/ha | Glyphosate g acid/L | Glyphosate g acid/1.3 L | 800SG g acid/kg | 800SG g/1.3 L | Water ml/canister |
| --- | --- | --- | --- | --- | --- |
| 45 | 0.70 | 0.91 | 800 | 1.14 | 1298.9 |
| 90 | 1.41 | 1.83 | 800 | 2.3 | 1297.7 |
| 180 | 2.81 | 3.65 | 800 | 4.6 | 1295.4 |
| 360 | 5.63 | 7.32 | 800 | 9.2 | 1290.8 |
| 450 | 7.03 | 9.1 | 800 | 11.4 | 1288.6 |

Herbicide Application

The annual ryegrass was at the early tillering stage (2 tillers) when sprayed with the herbicide treatments.

Herbicide formulations were applied using an enclosed laboratory track-sprayer fitted with three 110° flat fan nozzles ("Teejet"® XR11001-VS) spaced at 50 cm intervals across the boom. The boom moved along a fixed track at 6 km h−1, sprayed at a water volume of 64 L/ha with a pressure of 200 kPa.

There were eight replicates for each treatment.

Assessment

Seedlings were harvested 14 days after spray application by cutting foliage off at the base immediately prior to weighing on an "AND FX" 300 electronic balance (range 0-300 g).

Statistic Analysis

Data was analysed using an analysis of variance. 95% least significant differences (LSD) were calculated for the mean of each treatment.

Results

Ammonium Glyphosate Salt

There was little difference in the efficacy of any of the formulations (Table 13.4). There was a trend for the fresh weight of plants treated with the formulation containing tallow amine to be lower and at the 90 g/ha rate this was significantly lower.

TABLE 13.4

Fresh weight of annual ryegrass plants sprayed with ammonium glyphosate formulations at a range of concentrations in water. Numbers followed by the same letter are not significantly different ($P < 0.05$)

| Glyphosate Rate (g acid/ha) | Fresh Weight (g/plant) | | | | | |
| --- | --- | --- | --- | --- | --- | --- |
| | 800NH4-CB | 800NH4-CAPB | 800NH4-TA | 800NH4-AO | 800NH4-ADA | Bi Dri |
| 0 | 10.2i | 10.2i | 10.2i | 10.2i | 10.2i | 10.2i |
| 45 | 9.8i | 9.7i | 10.1i | 10.0i | 9.8i | 10.0i |
| 90 | 8.3h | 8.8h | 7.3g | 8.3h | 8.6h | 8.2h |
| 180 | 4.3ef | 4.2ef | 3.8e | 4.1ef | 4.8f | 4.2ef |
| 360 | 1.3bcd | 1.4cd | 1.0abcd | 1.4cd | 1.5d | 1.5d |
| 450 | 0.5a | 0.6abc | 0.4a | 0.6abc | 1.0abcd | 0.5ab |
| LSD (P = 0.05) | | | 0.91 | | | |

Conclusion

Figure 5:
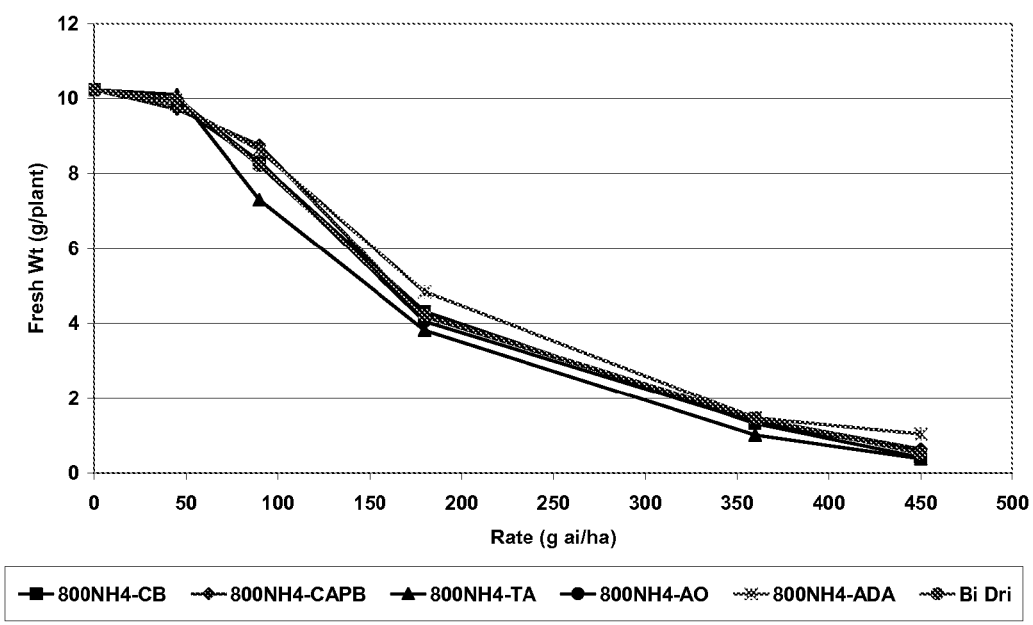
FIG. 5 illustrates a comparison of fresh weight of annual ryegrass treated with various ammonium glyphosphate formulations according to the present invention.

Although there were minor differences in efficacy all formulations were sufficiently effective to be commercially viable (FIG. 5).

Example 14

Comparison of the Efficacy of Three Glyphosate 900SG Variants with a Commercial Standard on Annual Ryegrass (Trial No. C)

Introduction

In this trial the efficacy of four surfactant variants applied in conjunction with a partially neutralized 900 g glyphosate acid/kg granule was compared with a commercial standard (Macphersons Glyphosate 840 Dri Flo and Macphersons Zest non ionic surfactant). The trial was undertaken in pots using annual ryegrass as the test species at the Agricultural and Food Precinct in Werribee, Victoria, Australia. The formulations according to the present invention were two-pack formulations—one pack was a glyphosate granule at 900 g/kg and the other pack was a surfactant formulation.

Materials and Methods

Plant Propagation

Annual ryegrass (*Lolium rigidum*) seeds (5/pot) were sown 13 Jun. 2010 to a depth of 10 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 20 days prior to spray application to more closely simulate field conditions and toughen up plants. After the application of herbicides the pots were returned to the greenhouse for an additional 14 days before plants were harvested for fresh weight.

Formulations

A sample of extruded granules was tested. These granules contained glyphosate acid and glyphosate ammonium salt to a concentration equivalent to 900 g glyphosate acid/kg.

The surfactants were; (i) an ethoxylated tallow amine plus a cocobetaine (TA+CB), (ii) a cocobetaine (CB), (iii) an amine oxide (AO) and (iv) an alkyl diamine alkoxylate (ADA) (Table 14.1). The efficacy of these formulations was compared with that of a commercial granule formulation Macphersons 840 Dri Flo (Dri Flo) which was used in conjunction with Zest. Zest contains a 530 g/L ethoxylated tallow amine plus 410 g/L ethoxylated alcohol.

Surfactant TA+CB was made by mixing equal parts of TA (a neat liquid) with CB (35% aqueous liquid as provided by the vendor)

Surfactant CB was a 35% aqueous liquid as provided by the vendor.

Surfactant AO was a 32-35% aqueous liquid as provided by the vendor.

Surfactant ADA was a wax formulated as described in example 3c (adjuvant pack, non-alkaline, solid).

TABLE 14.1

Surfactant formulations used in trial.

| Code | In product Surfactant System |
|---|---|
| TA + CB | Ethoxylated tallow amine + cocobetaine |
| CB | Cocobetaine |
| AO | Amine oxide |
| ADA | Alkyl diamine alkoxylate |
| Zest | Ethoxylated tallow amine + ethoxylated alcohol |

Herbicide and Surfactant in Spray Mix

The granules and surfactant were added at the required rates directly to the water in the spray canister to give a total spray weight of 1,300 g (Table 14.2, Table 14.3).

TABLE 14.2

Mixing Ratios Macphersons Dri Flo 840SG

| Glyphosate g acid/ha | Glyphosate g acid/1.3 L | Dri Flo g acid/kg | Bi Dri g/1.3 L | Zest ml/1.3L | Water ml/canister |
|---|---|---|---|---|---|
| 45 | 0.91 | 840 | 1.08 | 0.54 | 1298.4 |
| 90 | 1.83 | 840 | 2.18 | 1.09 | 1296.7 |
| 180 | 3.65 | 840 | 4.3 | 2.1 | 1293.6 |
| 360 | 7.32 | 840 | 8.7 | 4.3 | 1287.0 |
| 450 | 9.1 | 840 | 10.8 | 5.4 | 1283.8 |

TABLE 14.3

Mixing Ratios for glyphosate 900SG formulations.

| Glyphosate g acid/ha | Glyphosate g acid/1.3 L | 900SG g acid/kg | 900SG g/1.3 L | Surfactant ml or g/1.3 L | water ml/canister |
|---|---|---|---|---|---|
| 45 | 0.91 | 900 | 1.01 | 0.54 | 1298.5 |
| 90 | 1.83 | 900 | 2.03 | 1.09 | 1296.9 |
| 180 | 3.65 | 900 | 4.1 | 2.1 | 1293.8 |
| 360 | 7.32 | 900 | 8.1 | 4.3 | 1287.6 |
| 450 | 9.1 | 900 | 10.1 | 5.4 | 1284.5 |

Herbicide Spray Mix Application

The annual ryegrass was at the tillering stage (3 tillers) when sprayed with the herbicide treatments.

Herbicide formulations were applied using an enclosed laboratory track-sprayer fitted with three 110° flat fan nozzles ("Teejet"® XR11001-VS) spaced at 50 cm intervals across the boom. The boom moved along a fixed track at 6 km h−1, sprayed at a water volume of 64 L/ha with a pressure of 200 kPa.

There were eight replicates for each treatment.

Assessment

Seedlings were harvested 14 days after spray application by cutting foliage off at the base immediately prior to weighing on an "AND FX" 300 electronic balance (range 0-300 g).

Statistic Analysis

Data was analysed using an analysis of variance. 95% least significant differences (LSD) were calculated for the mean of each treatment.

Results

Figure 6:
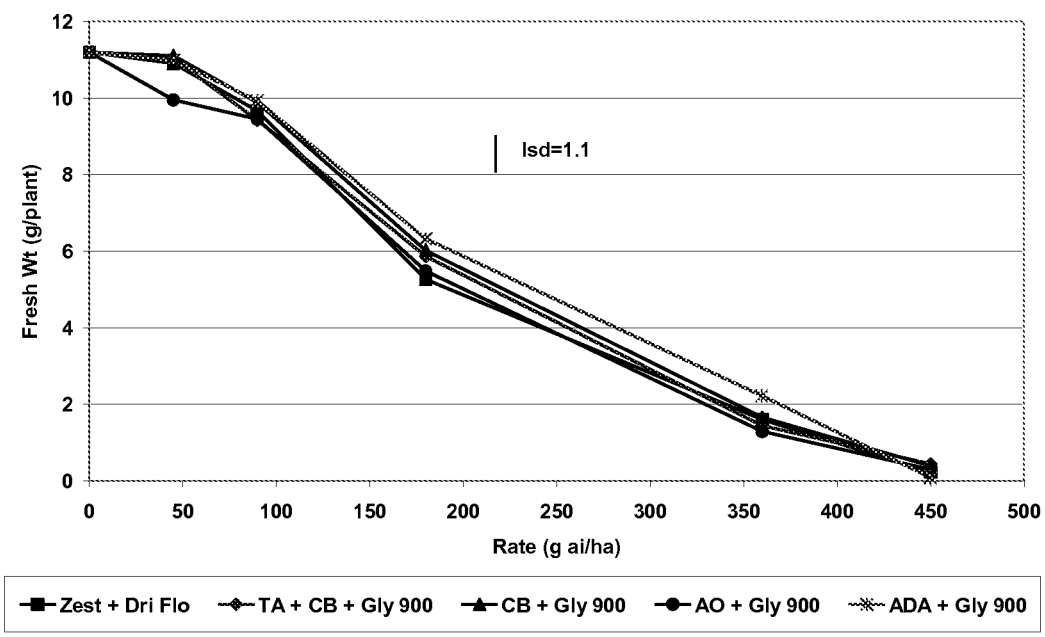
FIG. 6 illustrates fresh weight of annual ryegrass plants sprayed with formulations according to the present invention (900 g glyphosate acid equivalent/kg granule mixed with a range of surfactants in water. TA=ethoxylated tallow amine, CB=cocobetaine, AO=amine oxide, ADA=alkyl diamine alkoxylate). Dri Flo=Macphersons 840 Dri Flo which contains 840 g glyphosate acid equivalent as the ammonium salt.

There was no significant difference in the efficacy of any of the formulations (Table 14.4 and FIG. 6

TABLE 14.4

Fresh weight of annual ryegrass plants sprayed with a 900 g glyphosate acid equivalent/kg granule mixed with a range of surfactants in water.

| Glyphosate | Fresh Weight (g/plant) | | | | |
|---|---|---|---|---|---|
| Rate (g acid/ha) | Zest + Dri Flo | TA + CB + Gly 900 | CB + Gly 900 | AO + Gly 900 | ADA + Gly 900 |
| 0 | 11.2i | 11.2i | 11.2i | 11.2i | 11.2i |
| 45 | 10.9ghi | 11.02hi | 11.11i | 9.95fgh | 10.99hi |
| 90 | 9.67f | 9.42f | 9.88fg | 9.45f | 9.92fg |
| 180 | 5.26e | 5.86e | 6.02e | 5.48e | 6.32e |
| 360 | 1.6d | 1.4375cd | 1.66d | 1.29bcd | 2.22d |
| 450 | 0.23a | 0.44abc | 0.3875abc | 0.3ab | 0.09a |
| LSD (P = 0.05) | | | 1.1 | | |

TA = ethoxylated tallow amine,
CB = cocobetaine,
AO = amine oxide,
ADA = alkyl diamine alkoxylate.
Dri Flo = Macphersons 840 Dri Flo which contains 840 g glyphosate acid equivalent as the ammonium salt.
Numbers followed by the same letter are not significantly different (P < 0.05)

Conclusion

As there was no difference in efficacy all formulations were sufficiently effective to be commercially viable.

Example 15

Efficacy of Glyphosate 720SG (as Potassium Glyphosate+Acid) on Annual Ryegrass (Trial No. B/K+)

Introduction

The present inventors evaluated the efficacy of partially neutralized glyphosate formulations in a pot trial. The project was carried out at Agricultural and Food Precinct in Werribee, Victoria.
Materials and Methods
Plant Propagation Annual ryegrass (*Lolium rigidum*) seeds (5/pot) were sown 1 Mar. 2008 to a depth of 10 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 20 days prior to spray application to more closely simulate field conditions and toughen up plants. After the application of herbicides the pots were returned to the greenhouse for an additional 14 days before plants were harvested for fresh weight.
Formulations Five granule formulations were made using potassium glyphosate salt plus acid to a concentration of 720 g acid equivalent. The efficacy of these formulations was compared with that of a commercial standard granule formulation Macphersons 700Bi Dri (Bi Dri). The surfactant used in the Bi Dri formulation was a cocobetaine.

TABLE 15.1

Formulations used in trial

| Code | Glyphosate (g/kg) | In product Surfactant System |
|---|---|---|
| 720K-CB | 720 as K+ salt + acid | Cocobetaine |
| 720K-CAPB | | Cocoamidopropylbetaine |
| 720K-TA | | Ethoxylated tallow amine |
| 720K-AO | | Amine oxide |
| 720K-ADA | | Alkyl diamine alkoxylate |
| Bi Dri | 700 as $NH_4^+$ salt | Cocobetaine |

Herbicide and Spray Mix

The formulations were added at the required rates directly to the water in the spray canister to give a total spray weight of 1,300 g (Table 15.2, Table 15.3).

TABLE 15.2

Mixing Ratios Macphersons Bi Dri 700SG

| Glyphosate g acid/ha | Glyphosate g acid/L | Glyphosate g acid/1.3 L | Bi Dri. g acid/kg | Bi Dri g/1.3 L | Water ml/canister |
|---|---|---|---|---|---|
| 45 | 0.70 | 0.91 | 700 | 1.3 | 1298.7 |
| 90 | 1.41 | 1.83 | 700 | 2.6 | 1297.4 |
| 180 | 2.81 | 3.65 | 700 | 5.2 | 1294.8 |
| 360 | 5.63 | 7.32 | 700 | 10.5 | 1289.5 |
| 450 | 7.03 | 9.1 | 700 | 13.0 | 1287.0 |

TABLE 15.3

Mixing Ratios for glyphosate 720SG formulations.

| Glyphosate g acid/ha | Glyphosate g acid/L | Glyphosate g acid/1.3 L | 720SG g acid/kg | 720SG g/1.3 L | Water ml/canister |
|---|---|---|---|---|---|
| 45 | 0.70 | 0.91 | 720 | 1.26 | 1298.9 |
| 90 | 1.41 | 1.83 | 720 | 2.5 | 1297.7 |
| 180 | 2.81 | 3.65 | 720 | 5.1 | 1295.4 |
| 360 | 5.63 | 7.32 | 720 | 10.2 | 1290.8 |
| 450 | 7.03 | 9.1 | 720 | 12.6 | 1288.6 |

Herbicide Application

The annual ryegrass was at the early tillering stage (2 tillers) when sprayed with the herbicide treatments.

Herbicide formulations were applied using an enclosed laboratory track-sprayer fitted with three 110° flat fan nozzles ("Teejet"® XR11001-VS) spaced at 50 cm intervals across the boom. The boom moved along a fixed track at 6 km h−1, sprayed at a water volume of 64 L/ha with a pressure of 200 kPa.

There were eight replicates for each treatment.
Assessment

Seedlings were harvested 14 days after spray application by cutting foliage off at the base immediately prior to weighing on an "AND FX" 300 electronic balance (range 0-300 g).
Statistic Analysis Data was analysed using an analysis of variance. 95% least significant differences (LSD) were calculated for the mean of each treatment.
Results
Potassium Glyphosate Salt The efficacy of all potassium glyphosate/acid granules tended to be less efficacious than the ammonium glyphosate/acid granules. There was an obvious trend for better efficacy where the potassium glyphosate/acid was formulated with the ethoxylated tallow amine and for marginally inferior efficacy where it was formulated with the alkyl diamine alkoxylate (Table 15.4).

TABLE 15.4

Fresh weight of annual ryegrass plants sprayed with potassium glyphosate formulations at a range of concentrations in water. Numbers followed by the same letter are not significantly different (P < 0.05)

| Glyphosate Rate (g acid/ha) | Fresh Weight (g/plant) | | | | | |
|---|---|---|---|---|---|---|
| | 720K-CB | 720K-CAPB | 720K-TA | 720K-AO | 720K-ADA | Bi Dri |
| 0 | 10.2j | 10.2j | 10.2j | 10.2j | 10.2j | 10.2j |
| 45 | 9.9j | 10.1j | 10.1j | 10.2j | 10.4j | 10.0j |
| 90 | 8.5hi | 8.3ghi | 7.6g | 8.0gh | 8.9i | 8.2ghi |
| 180 | 5.1ef | 5.1ef | 4.1d | 4.5de | 5.5f | 4.2de |
| 360 | 1.3abc | 1.2abc | 1.1abc | 1.0abc | 1.7c | 1.5bc |
| 450 | 0.4a | 0.45a | 0.46a | 0.66ab | 0.93abc | 0.53a |
| LSD (P = 0.05) | 0.91 | | | | | |

Conclusion

Figure 7:
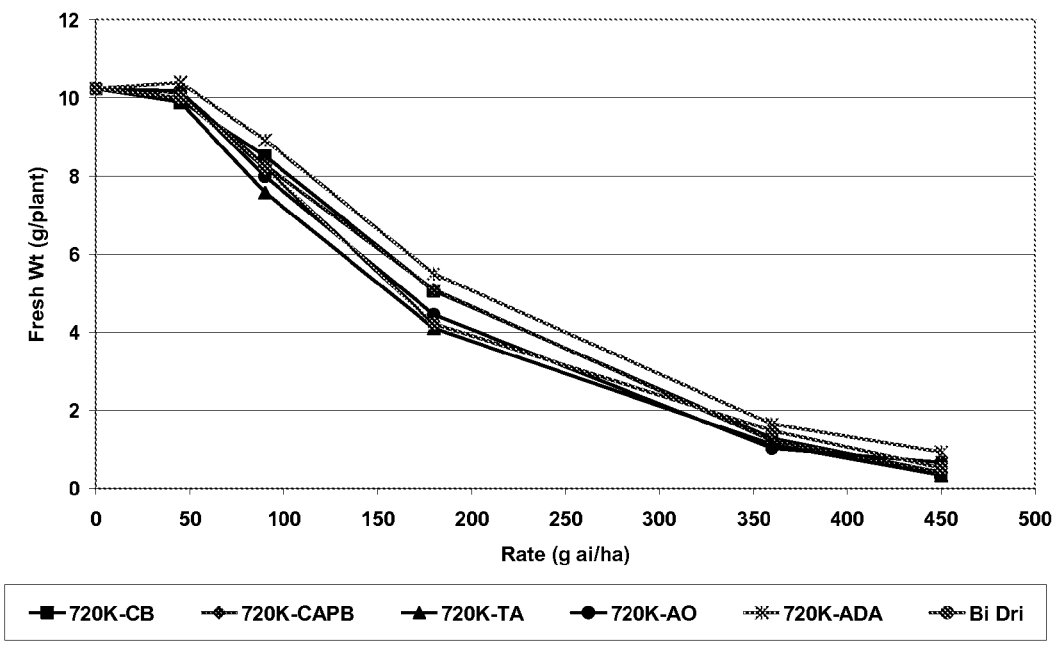
FIG. 7 illustrates fresh weight of annual ryegrass plants sprayed with various potassium glyphosate/acid formulations according to the present invention.

Although there were minor differences in efficacy all formulations were sufficiently effective to be commercially viable (FIG. 7).

The claims defining the invention are as follows:

1. A solid glyphosate formulation comprising glyphosate acid and further comprising at least one agriculturally acceptable salt of glyphosate,
   wherein the glyphosate acid and the at least one glyphosate salt are in admixture and
   wherein the mole ratio of glyphosate acid to total glyphosate moieties in the formulation is at least 10% and less than 50%;
   wherein the amount of glyphosate in the formulation calculated on an acid equivalent basis is at least 600 g/kg; and,
   wherein when 1 g of said solid glyphosate formulation is mixed with 100 g of 1 WHO hard water and passed through a 75 micron sieve, less than 0.02 g of residue (2%) is retained on the sieve.

2. The solid glyphosate formulation according to claim 1 wherein the mole ratio of glyphosate acid to total glyphosate moieties is less than 40%.

3. The solid glyphosate formulation according to claim 1, wherein the mole ratio of glyphosate acid to total glyphosate moieties is less than 30%.

4. The solid glyphosate formulation according to claim 1, wherein the formulation consists of granules.

5. The solid glyphosate formulation according to claim 4 wherein the granules are in the range of from 0.5 mm to 3 mm in length.

6. The solid glyphosate formulation according to claim 1, wherein the formulation consists of a powder.

7. The solid glyphosate formulation according to claim 1, comprising one or more adjuvants.

8. The solid glyphosate formulation according to claim 7 wherein the one or more adjuvants comprises a glyphosate synergising surfactant.

9. The solid glyphosate formulation according to claim 8 wherein the glyphosate synergising surfactant is selected from the group consisting of cocobetaine cocoamidopropylbetaine, tallowamine-15-ethoxylate, alkylpolyglycosides, and alkyldiamine alkoxylates.

10. The solid glyphosate formulation according to claim 8, wherein the weight ratio of glyphosate synergising surfactant to glyphosate acid equivalent is at least 50:700.

11. The solid glyphosate formulation according to claim 1, wherein the formulation is fully formulated.

12. The solid glyphosate formulation according to claim 1, wherein the at least one glyphosate salt comprises cations chosen from the group consisting of ammonium, sodium, potassium, ethanolammonium, diethanolammonium, triethanolammonium, propylammonium, isopropylammonium, and trimesium cations.

13. The solid glyphosate formulation according to claim 12 wherein the at least one glyphosate salt comprises ammonium cations.

14. The solid glyphosate formulation according to claim 13 wherein the at least one glyphosate salt is monoammonium glyphosate, and the weight ratio of glyphosate acid to total glyphosate moieties is in the range 9-50%.

15. The solid glyphosate formulation according to claim 13 wherein the amount of glyphosate in the formulation calculated on an acid equivalent basis is at least 730 g/kg.

16. The solid glyphosate formulation according to claim 13 wherein (a) the at least one glyphosate salt comprises monoammonium glyphosate; (b) the solid formulation is a fully formulated granule; and (c) the amount of glyphosate in the formulation calculated on an acid equivalent basis is at least 730 g/kg.

17. The solid glyphosate formulation according to claim 13 wherein the formulation is formulated in a two-pack formulation.

18. The solid glyphosate formulation according to claim 17 wherein the amount of glyphosate in the formulation calculated on an acid equivalent basis is at least 800 g/kg.

19. The solid glyphosate formulation according to claim 18 wherein the formulation is a granule.

20. The solid glyphosate formulation according to claim 12 wherein the at least one glyphosate salt comprises potassium cations.

21. The solid glyphosate formulation according to claim 12 wherein the at least one glyphosate salt comprises potassium and sodium cations.

22. The solid glyphosate formulation according to claim 12 wherein the at least one glyphosate salt comprises potassium and ammonium cations.

23. The solid glyphosate formulation according to claim 1, wherein when 3.5 g of solid glyphosate formulation is mixed with 100 g of 2 WHO hard water and passed through a 75 micron sieve, more than 0.03 g of residue is retained on the sieve.

24. The solid glyphosate formulation according to claim 1, wherein the solid glyphosate formulation meets a first criterion in which 1 g of solid glyphosate formulation is mixed with 100 g of 1 WHO hard water and passed through a 75 micron sieve with retention of less than 0.02 g residue on the sieve, and also meets a second criterion in which 3.5 g of solid glyphosate formulation is mixed with 100 g of 2 WHO hard water and passed through a 75 micron sieve to leave more than 0.03 g of residue on the sieve.

25. The solid glyphosate formulation according to claim 1, wherein adding 1% glyphosate acid equivalent of the solid glyphosate formulation to distilled water provides a final pH in the range 1.5-3.7.

26. A method of removing unwanted foliage comprising administering a diluted form of a solid glyphosate formulation according to claim 1 to said foliage.

27. A method of preparing a solid glyphosate formulation comprising glyphosate acid and potassium glyphosate wherein the mole ratio of glyphosate acid to total glyphosate moieties in the formulation is at least 10% and less than 50%, wherein the amount of glyphosate in the formulation calculated on an acid equivalent basis is at least 600 g/kg, and, wherein when 1 g of said solid glyphosate formulation is mixed with 100 g of 1 WHO hard water and passed through a 75 micron sieve, less than 0.02 g of residue (2%) is retained on the sieve, said method comprising partially neutralising the glyphosate acid with potassium hydroxide.

28. A method according to claim 26, wherein said glyphosate acid is in the form of glyphosate 85% wet cake.

29. The solid glyphosate formulation according to claim 8, wherein the weight ratio of glyphosate synergising surfactant to glyphosate acid equivalent is at least 100:700.

30. The solid glyphosate formulation according to claim 13, wherein the at least one glyphosate salt is monoammonium glyphosate, and the weight ratio of glyphosate acid to total glyphosate moieties is in the range 15-40%.

31. The solid glyphosate formulation according to claim 13, wherein the at least one glyphosate salt is monoammonium glyphosate, and the weight ratio of glyphosate acid to total glyphosate moieties is in the range 22-35%.

32. The solid glyphosate formulation according to claim 13, wherein the amount of glyphosate in the formulation calculated on an acid equivalent basis is at least 750 g/kg.

33. The solid glyphosate formulation according to claim 13, wherein the amount of glyphosate in the formulation calculated on an acid equivalent basis is at least 780 g/kg.

34. The solid glyphosate formulation according to claim 13, wherein the amount of glyphosate in the formulation calculated on an acid equivalent basis is at least 800 g/kg.

35. The solid glyphosate formulation according to claim 13 wherein (a) the at least one glyphosate salt comprises monoammonium glyphosate; (b) the solid formulation is a fully formulated granule; and (c) the amount of glyphosate in the formulation calculated on an acid equivalent basis is at least 750 g/kg.

36. The solid glyphosate formulation according to claim 13 wherein (a) the at least one glyphosate salt comprises monoammonium glyphosate; (b) the solid formulation is a fully formulated granule; and (c) the amount of glyphosate in the formulation calculated on an acid equivalent basis is at least 800 g/kg.

37. The solid glyphosate formulation according to claim 17, wherein the amount of glyphosate in the formulation calculated on an acid equivalent basis is at least 850 g/kg.

38. The solid glyphosate formulation according to claim 17, wherein the amount of glyphosate in the formulation calculated on an acid equivalent basis is at least 880 g/kg.

39. The solid glyphosate formulation according to claim 17, wherein the amount of glyphosate in the formulation calculated on an acid equivalent basis is at least 900 g/kg.

40. The solid glyphosate formulation according to claim 20, wherein the amount of glyphosate in the formulation calculated on an acid equivalent basis is at least 650 g/kg.

41. The solid glyphosate formulation according to claim 20, wherein the amount of glyphosate in the formulation calculated on an acid equivalent basis is at least 680 g/kg.

42. The solid glyphosate formulation according to claim 20, wherein the amount of glyphosate in the formulation calculated on an acid equivalent basis is at least 700 g/kg.

43. The solid glyphosate formulation according to claim 1, wherein adding 1% glyphosate acid equivalent of the solid glyphosate formulation to distilled water provides a final pH in the range 2-3.

44. The solid glyphosate formulation according to claim 8, wherein the weight ratio of glyphosate synergising surfactant to glyphosate acid equivalent is at least 80:700.

45. A method of preparing a solid glyphosate formulation comprising glyphosate acid and ammonium glyphosate wherein the mole ratio of glyphosate acid to total glyphosate moieties in the formulation is at least 10% and less than 50%, wherein the amount of glyphosate in the formulation calculated on an acid equivalent basis is at least 600 g/kg, and wherein when 1 g of said solid glyphosate formulation is mixed with 100 g of 1 WHO hard water and passed through a 75 micron sieve, less than 0.02 g of residue (2%) is retained on the sieve, said method comprising the step of mixing the ammonium glyphosate with the glyphosate acid.

46. A method of preparing a solid glyphosate formulation according to claim 27 wherein said formulation further comprises sodium glyphosate, said method comprising an additional step of partially neutralising the glyphosate acid with sodium hydroxide.

* * * * *